(12) United States Patent
Charles, Jr. et al.

(10) Patent No.: US 7,203,274 B2
(45) Date of Patent: Apr. 10, 2007

(54) METHOD AND APPARATUS FOR MULTIPLE-PROJECTION, DUAL-ENERGY X-RAY ABSORPTIOMETRY SCANNING

(75) Inventors: Harry K. Charles, Jr., Laurel, MD (US); Thomas J. Beck, Baltimore, MD (US); Howard S. Feldmesser, Columbia, MD (US); Thomas C. Magee, Sykesville, MD (US)

(73) Assignee: The Johns Hopkins University, Baltimore, MD (US)

( * ) Notice: Subject to any disclaimer, the term of this patent is extended or adjusted under 35 U.S.C. 154(b) by 82 days.

(21) Appl. No.: 10/399,617

(22) Filed: Aug. 14, 2003

(65) Prior Publication Data

US 2004/0028181 A1    Feb. 12, 2004

Related U.S. Application Data

(60) Provisional application No. 60/242,740, filed on Oct. 24, 2000, provisional application No. 60/246,679, filed on Nov. 8, 2000.

(51) Int. Cl.
*G01N 23/06* (2006.01)
(52) U.S. Cl. .......................................... 378/54; 378/62
(58) Field of Classification Search ............ 378/54–56, 378/4, 9, 51, 62, 193, 196, 197, 5
See application file for complete search history.

(56) References Cited

U.S. PATENT DOCUMENTS 3,924,133 A * 12/1975 Reiss ........................ 378/62
4,417,353 A    11/1983 Groh et al.
5,040,199 A *  8/1991 Stein ........................ 378/56
5,432,834 A     7/1995 Gershman
5,570,403 A * 10/1996 Yamazaki et al. ............. 378/5
5,661,774 A     8/1997 Gordon et al.
5,748,705 A     5/1998 Stein et al.
5,762,608 A     6/1998 Warne et al.
5,796,802 A     8/1998 Gordon
5,838,765 A    11/1998 Gershman et al.
6,438,201 B1 * 8/2002 Mazess et al. ................ 378/56

FOREIGN PATENT DOCUMENTS

EP    1 044 649 A1    4/2000
WO    WO 94/10908    5/1994

* cited by examiner

*Primary Examiner*—Courtney Thomas
(74) *Attorney, Agent, or Firm*—Francis A. Cooch

(57) ABSTRACT

Methods and apparatuses for advanced, multiple-projection, dual-energy X-ray absorptiometry scanning systems include combinations of a conical collimator; a high-resolution two-dimensional detector; a portable, power-capped, variable-exposure-time power supply; an exposure-time control element; calibration monitoring; a three-dimensional anti-scatter-grid; and a gantry-gantry base assembly that permits up to seven projection angles for overlapping beams. Such systems are capable of high precision bone structure measurements that can support three dimensional bone modeling and derivations of bone strength, risk of injury, and efficacy of countermeasures among other properties.

19 Claims, 15 Drawing Sheets

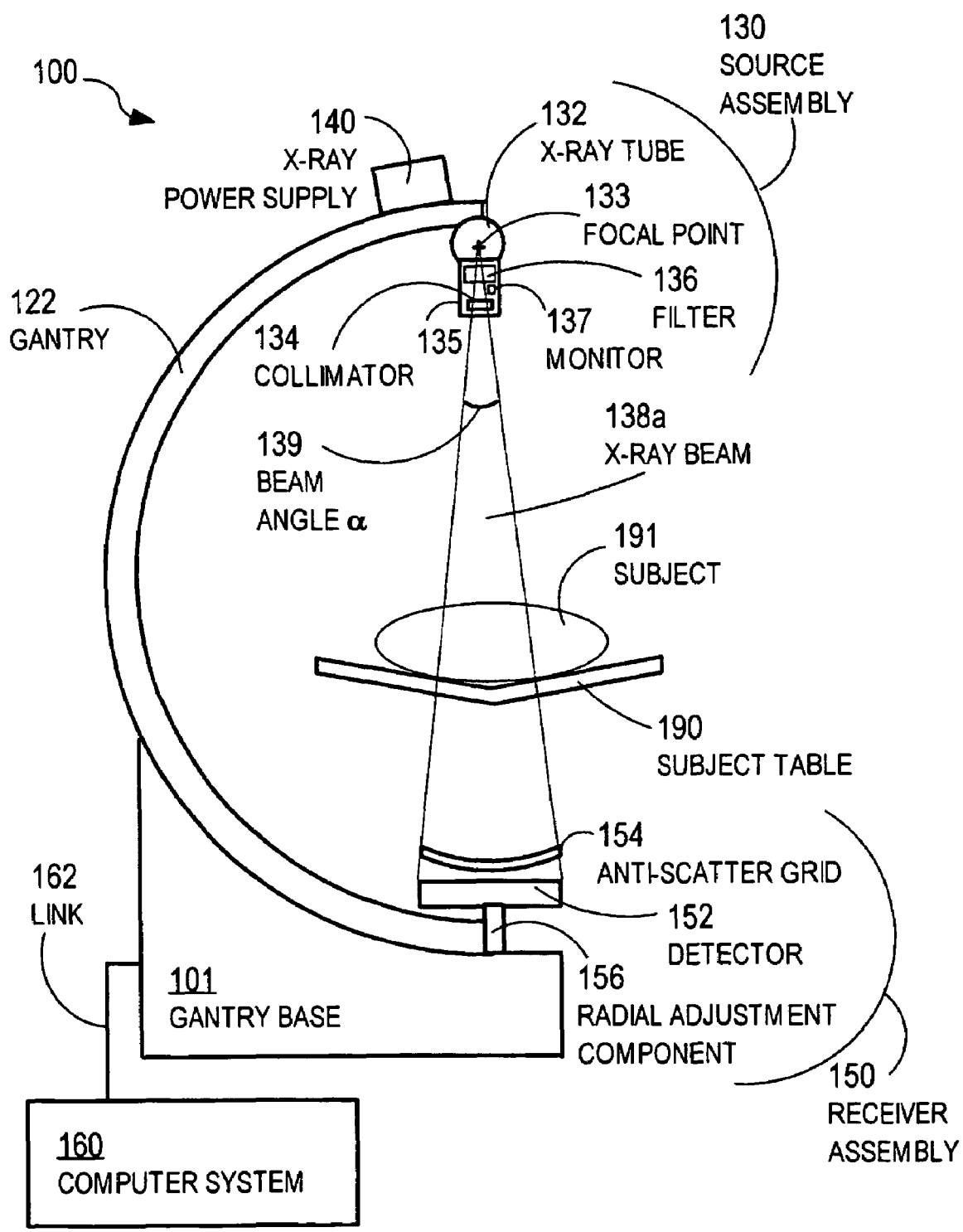

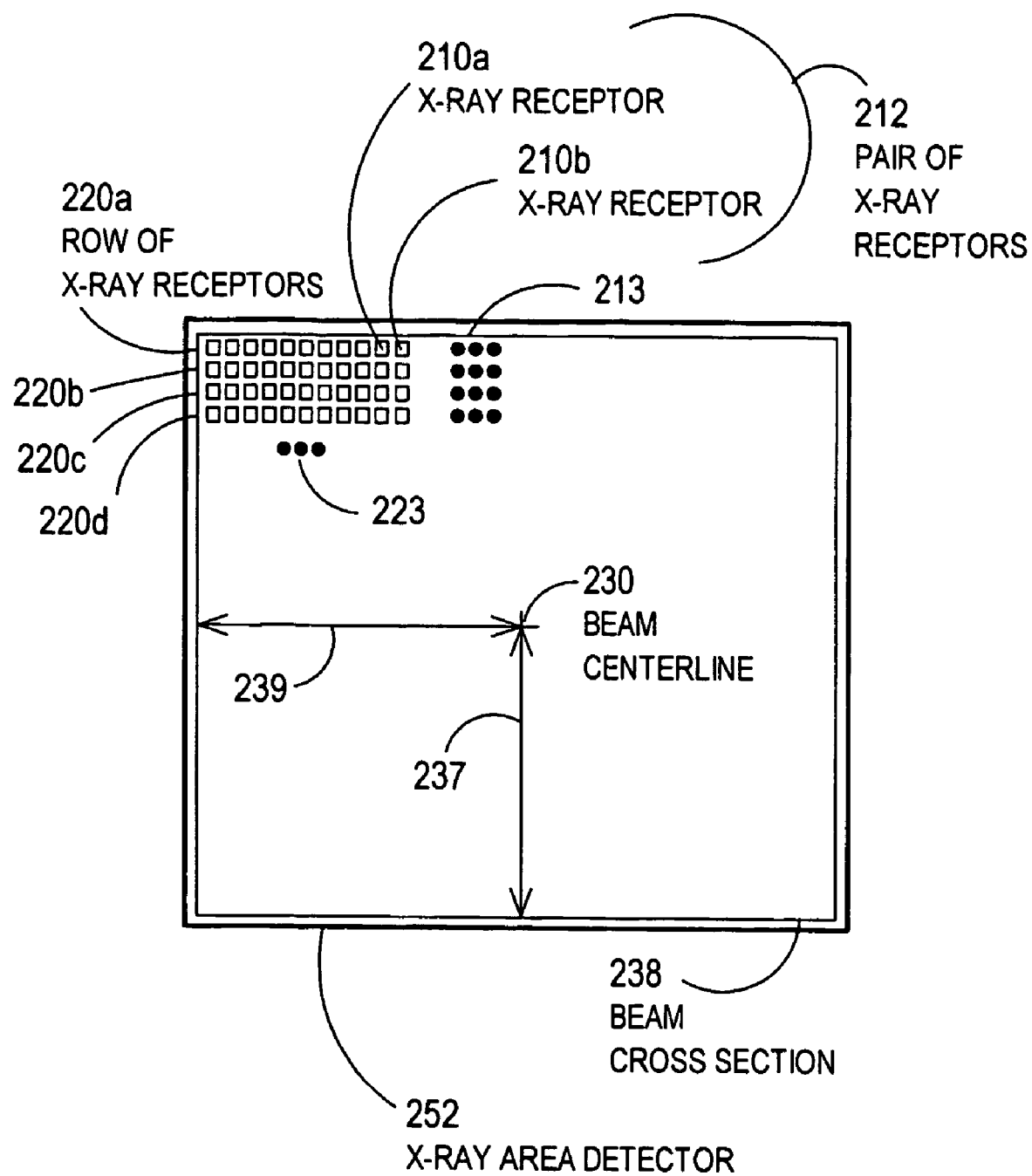

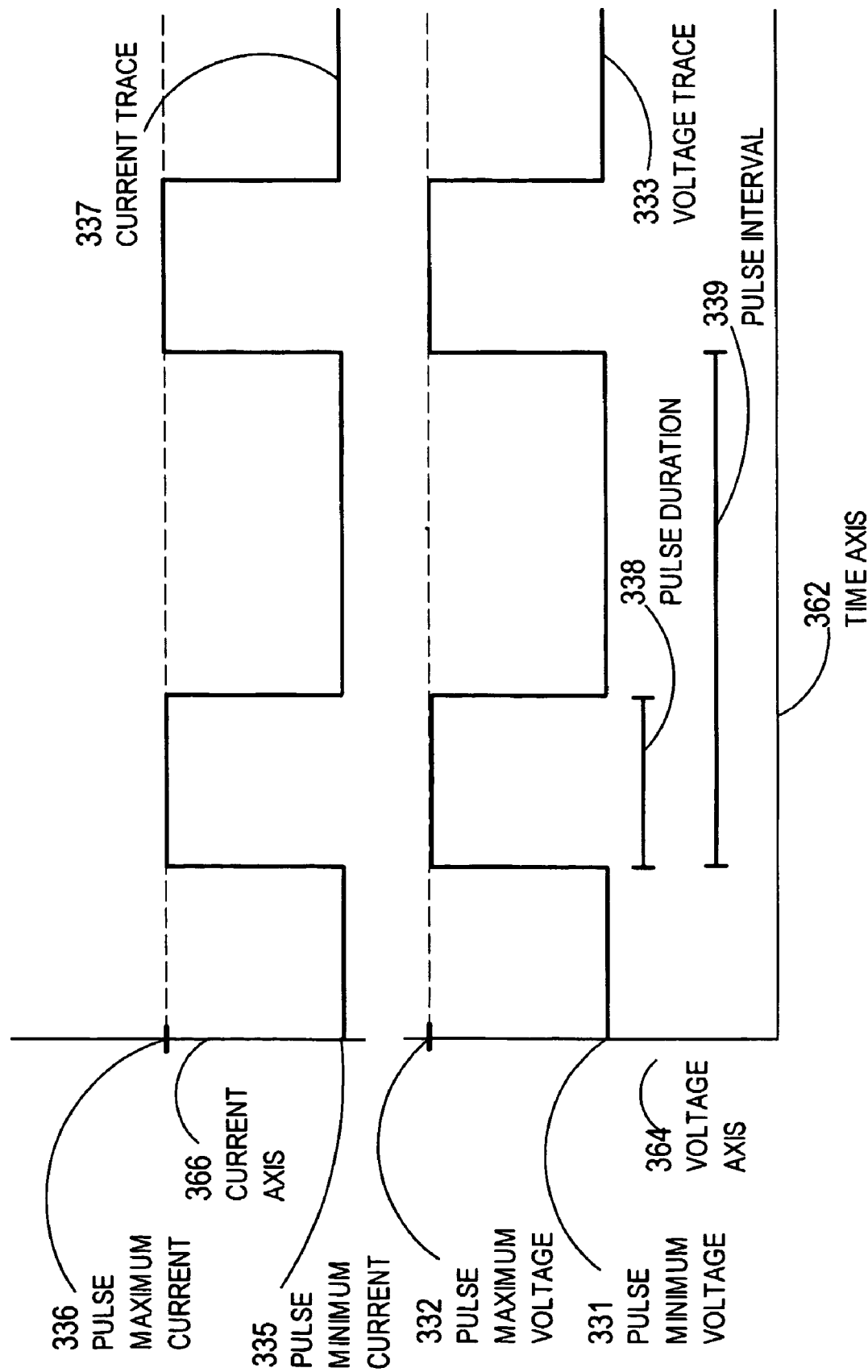

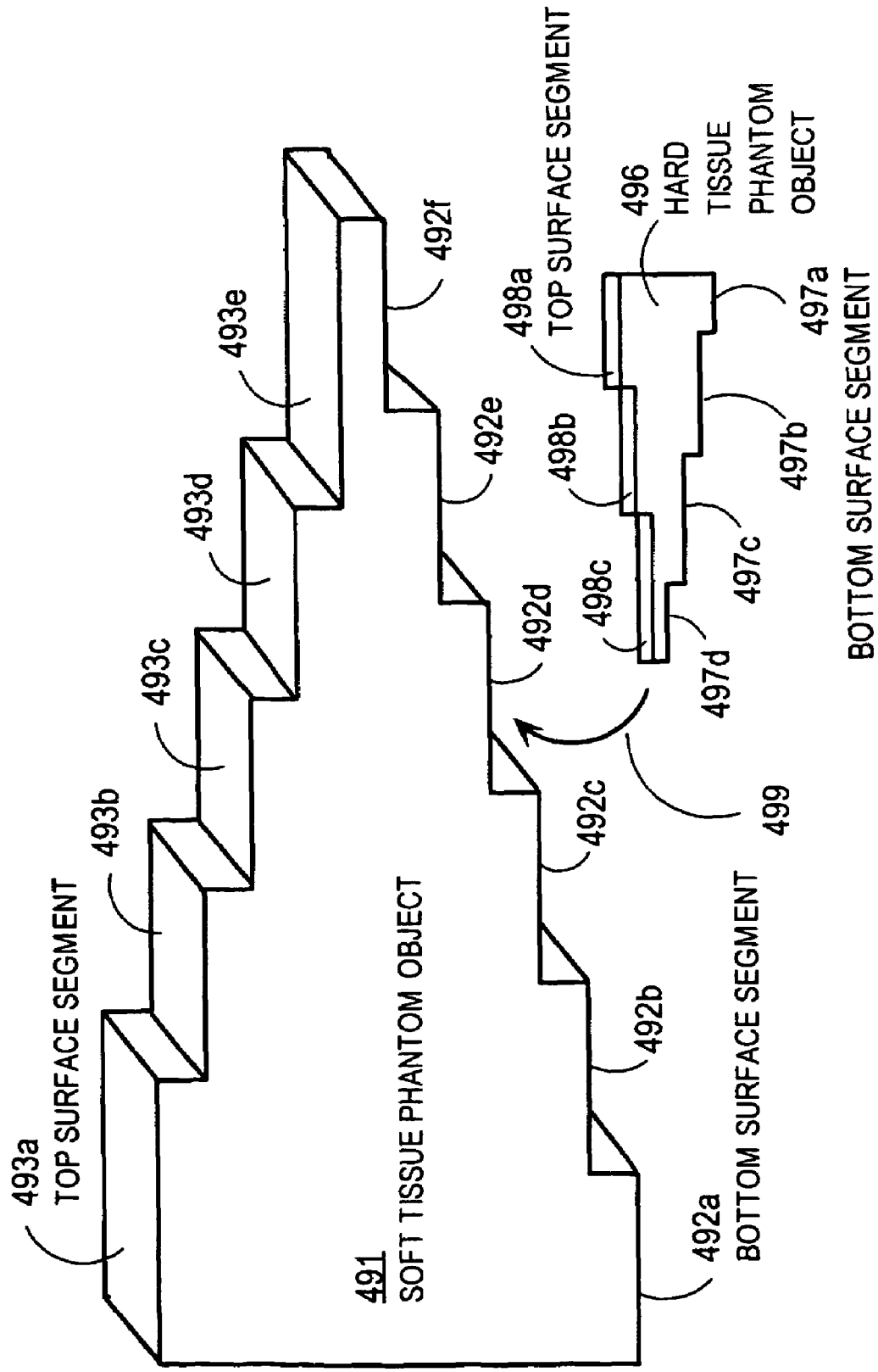

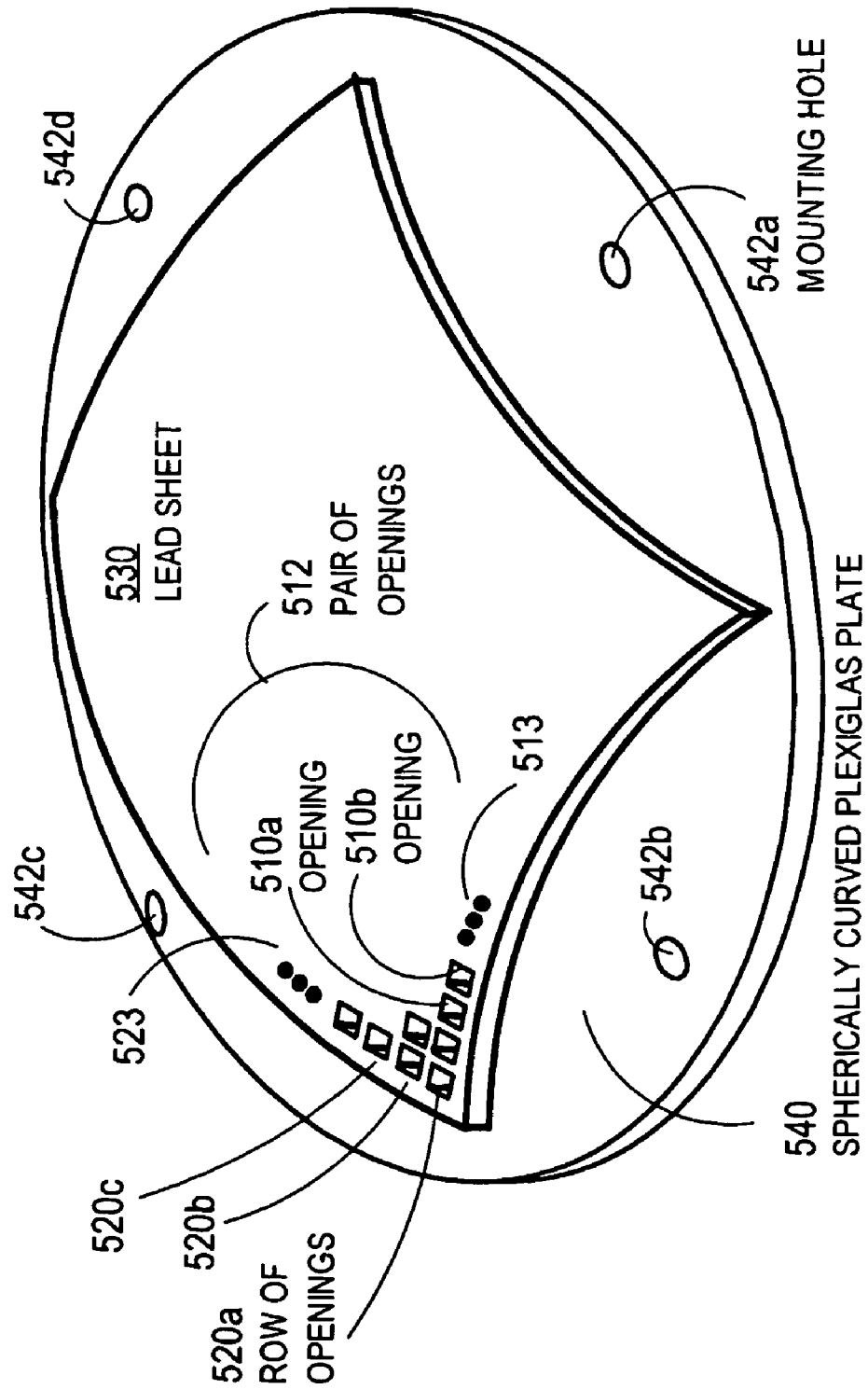

METHOD AND APPARATUS FOR MULTIPLE-PROJECTION, DUAL-ENERGY X-RAY ABSORPTIOMETRY SCANNING

CROSS-REFERENCE TO RELATED APPLICATIONS

This application claims the benefit of U.S. provisional application No. 60/242,740, filed on Oct. 24, 2000, which is hereby incorporated by reference in its entirety. This application also claims the benefit of U.S. provisional application No. 60/246,679, filed on Nov. 8, 2000, which is hereby incorporated by reference in its entirety.

STATEMENT OF GOVERNMENTAL INTEREST

This invention was made with Government support under Cooperative Agreement NCC 9-58 between the National Aeronautics and Space Administration (NASA) Johnson Space Center, Houston, Tex. and the National Space Biomedical Research Institute (NSBRI). The Government has certain rights in the invention.

BACKGROUND OF THE INVENTION

1. Field of the Invention

The present invention relates to dual-energy x-ray absorptiometry; and, in particular to an instrument for high-precision, calibrated, absorption measurements that support computations of bone structure, strength and risk of fracture.

2. Description of the Related Art

The system of bones and skeletal muscles provides structure to a human or animal body, and provides the capability to carry out activities. Bone provides the basic structural integrity of the body that carries forces and furnishes a framework for muscle.

Experience with bed rest subjects, astronauts and cosmonauts indicates that the magnitudes and patterns of bone tissue loss are extremely variable from one individual to the next, and also between different body regions. Little mass appears to be lost from the upper extremities during weightlessness; whereas the rate of mass loss from the vertebrae, pelvis, and proximal femurs of astronauts average between 1 percent and 1.6 percent per month. The rate of mass loss from those sites in postmenopausal woman average between 0.8 percent and 1.3 percent per year—a substantially lower rate of loss.

Recent evidence shows that there are important differences between the ways that bone is lost in aging on earth compared to changes observed during space flight. On earth, the skeleton is continually loaded during normal activities. Load causes mechanical strains within the bone, which tend to be greatest on the subperiosteal surface, the connective tissue with bone forming cells attached to the surface (cortex) of the bone. In response, more new bone mass forms on the cortex. Simultaneously, the normal turnover of bone accompanying the aging process causes some net loss of bone from endocortical (inside the cortex) and internal surfaces. In long bones, the net loss under loading causes skeletal strains to increase most on the subperiosteal surface, not at the internal surfaces where the bone loss occurred. Because it takes less new bone on the subperiosteal surface to compensate for bone loss from internal surfaces, strength can be maintained in the presence of net bone loss.

During space flight, loading is practically absent on the lower skeleton. Not only does bone loss accelerate under diminishing loading, but evidence from cosmonaut data suggests that the compensatory changes are absent as well. This means that astronauts may be at a greater risk of fracture for the same loss of bone mass. Therefore it is important not only to determine bone mass, but also to determine the geometrical configuration of the bone structure. Bones loss countermeasures can be developed to increase the loading on the lower skeleton. The efficacy of such countermeasures is better determined individually, based on the geometrical configuration of the individual's bone structure before and after the countermeasures, than by analyzing bone breakage statistics over a large population of astronauts. There is simply not a large population of astronauts.

Furthermore, the determination of bone structure is useful for screening a population and monitoring treatments of osteoporosis in postmenopausal women, elderly men and other susceptible individuals.

Loading and bone loss countermeasures can also be assessed through the measurements of muscle mass in a living human. Therefore it an advantage for a scanning device to also distinguish fat from muscle in soft tissue. Soft tissue excludes bone tissue.

There are several methods for determining bone mineral density (BMD), bone structure, and soft tissue components. These methods include computed tomography (CT), magnetic resonance imaging (MRI), ultrasound, and dual-energy x-ray absorptiometry (DXA).

While a CT unit can image and measure the geometrical characteristics of bone and soft tissue, it is not well suited for use in space because of its high radiation dose per scan. In addition, a CT unit capable of performing total body scans is extremely massive, weighing thousands of pounds. This great weight renders such units impractical for portable and space flight use. In addition, the high cost and large size place such units beyond the reach of small earthbound clinics, which might otherwise administer osteoporosis screening and treatment monitoring. An MRI unit is excellent for imaging soft tissues, for example to distinguish fat from muscle. However, an MRI unit suffers from a similar size and weight disadvantage. An MRI unit capable of performing whole body scans consumes significant power, generates large magnetic fields, and weighs tens of thousands of pounds.

Commercial scanners use dual-energy x-ray absorptiometry (DXA) or ultrasound to yield measurements of bone mineral density (BMD) that are regional averages. However, regional averages obscure structural details, and thus are not precise enough to deduce bone strength. Such systems do not predict risk of breakage. Furthermore, ultrasound devices have not been used successfully for the quantification of muscle mass.

In addition, commercial DXA devices consume too much energy for portable use. Furthermore DXA scanners employ ionizing radiation, which can pose a radiation risk to astronauts confined to operate in small spaces in the vicinity of a DXA device.

Based on the foregoing description, there is a clear need for a portable device that provides measurements of bone structure, fat tissue mass and lean tissue mass.

In particular, there is a need for a device that provides measurements of bone structure, fat tissue mass and lean tissue mass and that meets space flight constraints on size, weight, power consumption and radiation leakage.

Furthermore, there is a need for a system that yields a risk of injury including bone breakage.

SUMMARY OF THE INVENTION

According to one aspect of the invention, a dual-energy x-ray absorptiometry apparatus is provided that includes a first source of a first conical beam of x-rays having photon energies in a first range of photon energies and a second source of a second conical beam of x-rays having photon energies in a second range of photon energies. The second range is different from the first range of photon energies. The second beam is co-located with the first beam. Also included is an x-ray receiver having an area x-ray detector for detecting x-ray intensity at a plurality of receptors distributed over an area having a length and a width. A subject table that is substantially transparent to x-rays is also included. The first conical beam intersects the subject table and impinges on the area x-ray detector.

According to an embodiment of this aspect, the x-ray receiver also includes a three dimensional anti-scatter grid with a plurality of holes.

According to another aspect of the invention, a dual-energy x-ray absorptiometry apparatus includes a source of a beam having a series of constant pulses. Each pulse has x-ray photon energies in a range of photon energies. An x-ray detector is included for detecting x-ray intensity and providing first data indicating a number of photons received at the detector during each pulse. An exposure control component is included for determining a number of pulses in the first series of constant pulses based on the first data.

According to another aspect of the invention, a dual-energy x-ray absorptiometry apparatus includes a source of a beam having x-ray photon energies in a range of photon energies. An x-ray detector is included for detecting x-ray intensity after the beam has passed through a subject. A monitor with a receptor coupled to a calibration material is included for providing monitoring data indicating x-ray intensity attenuated by the calibration material at the source over time. A calibration-monitoring component determines whether calibration of the apparatus has degraded below a threshold accuracy based on the monitoring data.

According to another aspect of the invention, a dual-energy x-ray absorptiometry apparatus includes a first source of a first beam of x-rays and a second source of a second beam of x-rays. The first beam has photon energies in a first range of photon energies. The second beam has photon energies in a second range of photon energies different from the first range of photon energies. The second beam co-located with the first beam. An x-ray receiver is included for detecting x-ray intensity. A subject table substantially transparent to x-rays is also included. A gantry is moveably connected to a gantry base. The gantry is fixed to the first source, the second source and the x-ray receiver. The gantry base is configured to move the gantry to multiple gantry positions. The first beam intersects the subject table at multiple angles corresponding to the multiple gantry positions. The first beam impinges on the x-ray receiver for each of the positions. The first beam at one of the angles substantially overlaps, in a volume above the subject table, the first beam at two or more neighboring angles. The volume would be occupied by a subject disposed on the subject table.

According to another aspect of the invention, a power supply for a dual-energy x-ray absorptiometry apparatus includes a direct current source providing direct current, Is, at voltage, Vs, up to a particular peak power, Pmax. A pulse forming network (PFN) circuit is connected to receive the direct current, Is, from the power source. The PFN includes one or more capacitors to form a series of pulses. Each pulse has a pulse current Ip and pulse voltage Vp for a pulse duration Tp repeated at a pulse time interval Ti. The quantity Ip*Vp*Tp/Ti is less than Pmax. A pulse transformer assembly is connected to receive the series of pulses and is configured to step the pulse voltage, Vp, up to an x-ray tube voltage, Vx, between a first cathode and an anode of an x-ray tube. Vx is larger than Vp.

According to another aspect of the invention, an anti-scatter grid for an x-ray absorptiometry apparatus includes a sheet of a heavy metal shaped with openings. The heavy metal sheet has a width and a length that substantially covers an area x-ray detector of the x-ray absorptiometry apparatus. Each opening of the plurality of openings has sidewalls substantially perpendicular to a top surface of the heavy metal sheet. Each opening has a maximum opening size in the top surface selected so that an x-ray having an angle of incidence on the top surface that deviates from a direction perpendicular to the top surface by a deviation angle greater than a particular acceptance angle strikes a sidewall of the opening.

According to another aspect of the invention, a method for fabricating an anti-scatter grid for a dual-energy x-ray absorptiometry apparatus includes cutting cross slots onto an electrode to produce regularly spaced posts in a two-dimensional array. The posts are sunk into a lead foil. Electrical discharge machining (EDM) is performed to burn openings through the lead foil at locations corresponding to the posts. The openings are widened by displacing the posts a distance smaller than a spacing between posts, and performing electrical discharge machining to widen the plurality of openings.

According to another aspect of the invention, a method for fabricating an anti-scatter grid for a dual-energy x-ray absorptiometry apparatus includes cutting cross slots onto a copper electrode to produce regularly spaced posts in a two-dimensional array. Molten lead is poured over the electrode to a depth less than a height of the posts. The lead is allowed to solidify. The copper is chemically removed to leave a lead sheet with openings corresponding to the posts.

According to another aspect of the invention, a method for operating a dual-energy x-ray absorptiometry apparatus includes obtaining a pair of images at each of a plurality of projection angles for each of one or more longitudinal positions along a subject. A first image of the pair is obtained using a first source of x-rays having a first range of photon energies. A second image of the pair is obtained using a second source of x-rays having a second range of photon energies. Each image has at least two pixels per millimeter. A three-dimensional model of a bone is constructed based on several pairs of the images obtained.

According to another aspect of the invention, a method for calibrating a dual-energy x-ray absorptiometry apparatus includes placing a phantom subject of a tissue calibration material on a subject table. A pair of attenuation images is obtained. A first image of the pair is obtained using a first source of x-rays having a first range of photon energies. A second image of the pair is obtained using a second source of x-rays having a second range of photon energies. Each image has at least two pixels per millimeter. Coefficients are determined based on the pair of images. The coefficients are for a polynomial that produces thickness of the calibration material at each pixel based on attenuation at that pixel in the pair of attenuation images.

These techniques allow an advanced, multiple-projection, dual-energy x-ray absorptiometry scanning system to be developed that includes combinations of 1) a conical collimator; 2) a high-resolution two-dimensional detector; 3) a portable, power-capped, variable-exposure-time power supply; 4) an exposure-time control element; 5) calibration monitoring; 6) a three-dimensional anti-scatter-grid; and 7) a gantry-gantry base assembly that permits up to seven projection angles for overlapping beams. Such systems are capable of high precision bone structure measurements that can support derivations of strength, risk of injury, and efficacy of countermeasures among other properties.

BRIEF DESCRIPTION OF THE DRAWINGS

The present invention is illustrated by way of example, and not by way of limitation, in the figures of the accompanying drawings and in which like reference numerals refer to similar elements and in which:

FIG. 1A is a block diagram illustrating structural components of an apparatus for multiple-projection, dual-energy x-ray absorptiometry, according to an embodiment.

FIG. 2B is a block diagram illustrating an area detector for a dual-energy x-ray absorptiometry apparatus, according to an embodiment;

FIG. 3B is a timeline chart illustrating output current and voltage from a pulse forming network for the portable power supply, according to an embodiment;

FIG. 4B is a block diagram illustrating two phantom objects used together as a subject to calibrate the x-ray absorption measurements and check the exposure control system, according to an embodiment;

FIG. 5A is a block diagram illustrating a three-dimensional anti-scatter grid, according to an embodiment;

DETAILED DESCRIPTION

Figure 1B:
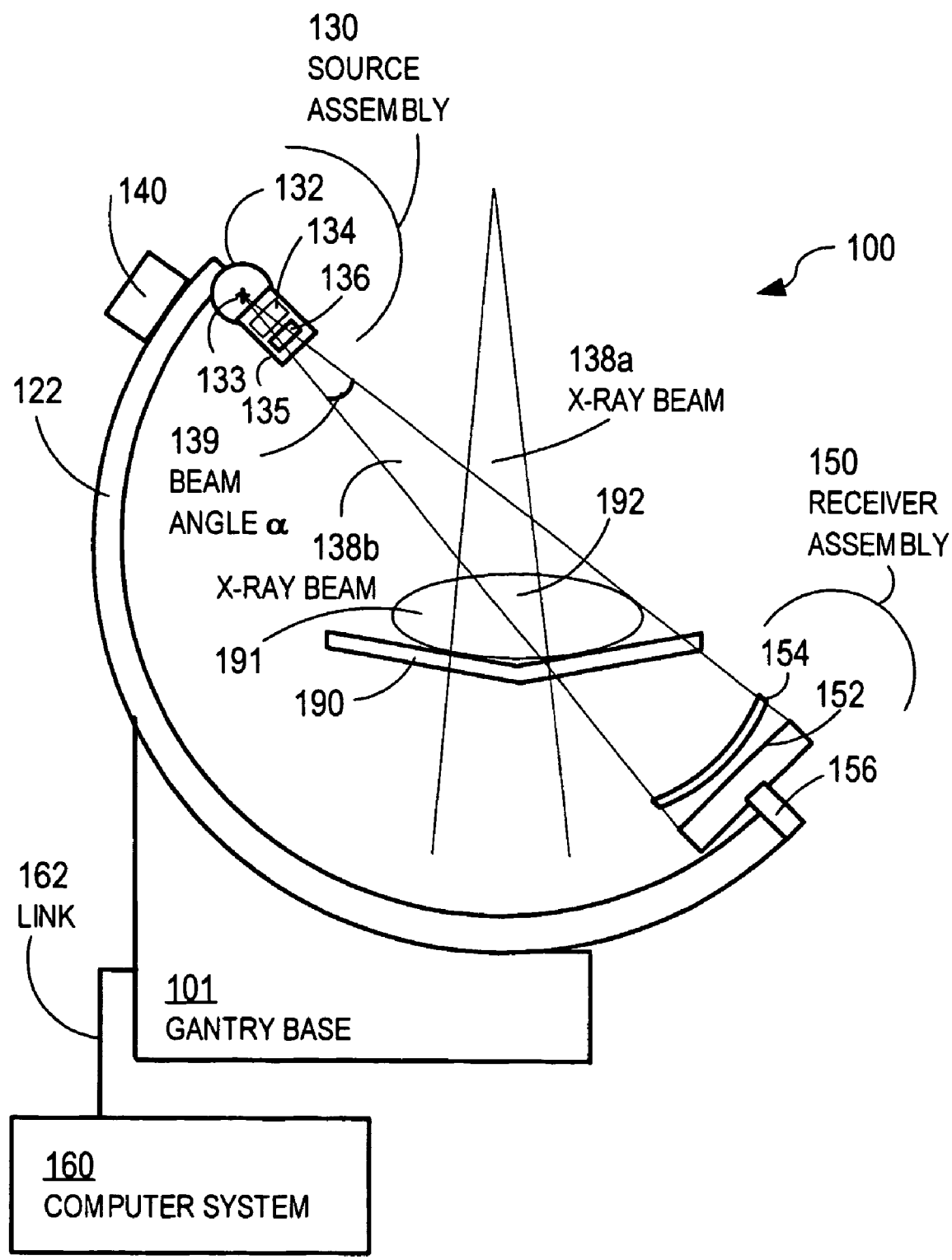
FIG. 1B is a block diagram illustrating the apparatus of FIG. 1A when configured for a different projection angle.

A method and apparatus for multiple-projection, dual-energy x-ray absorptiometry is described. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

1. Structural Overview

FIG. 1A is a block diagram illustrating structural components of an apparatus 100 for multiple-projection, dual-energy x-ray absorptiometry, according to an embodiment. The cross section of FIG. 1A defines an X-Z plane in which Z is the vertical dimension and X is the horizontal dimension. A horizontal dimension extending out of the page, perpendicular to the X-Z plane, is the Y dimension.

The apparatus includes a gantry 122 shaped to hold an x-ray source assembly 130 in fixed relation to a receiver assembly 150. An x-ray beam 138a is emitted from the source assembly 130 to the receiver assembly 150. In an example embodiment, a centerline of the beam 138a lies in the X-Z plane. The gantry is moveably attached to a gantry base 101 so that the source assembly 130, the receiver assembly 150, and the beam 138a centerline rotate in the X-Z plane about an axis line in the Y dimension. The rotation preserves the distance and relative directions between the source assembly 130 and the receiver assembly 150. In other embodiments, the locations of the source assembly 130 and the receiver assembly 150 on the gantry are exchanged, so that the source lies below the subject and the receiver lies above. In other embodiments, the gantry has other shapes, such as an annular shape.

A subject table 190, transparent to x-rays, is disposed between the source assembly 130 and receiver assembly 150 in the X-Z plane. The subject table 190 supports a subject 191 during operation of the apparatus 100. Either the subject table 190 or the gantry base 101 or both are configured to translate in the Y dimension so that different portions of the subject 191 intersect the X-Z plane. In some embodiments, the subject table may also rotate in an X-Y plane about an axis line in the Z dimension. In other embodiments, the receiver assembly employs a detector large enough in the Y dimension so that the subject table is not translated in the Y direction.

The gantry is connected to a computer system 160 by a communications link 162. Through link 162, the computer system 160 controls the motion of the gantry 122 and gantry base 101, controls the operation of the source assembly 130, and receives data from a detector 152 of the receiver assembly 150. In some embodiments, the computer system also controls the movement of the subject table through link 162 or another link, not shown.

The source assembly 130 includes an x-ray power supply 140, an x-ray tube 132 and an x-ray beam-forming component 135. X-rays are electromagnetic waves. A discrete quantum of an electromagnetic wave is a photon. An x-ray with frequency (v) has a photon energy (E) proportional by Plank's constant h; that is, E=h v.

In the x-ray tube, high-energy electrons from a heated filament collide with a material (at a positively charged anode) where the electrons are suddenly decelerated to produce x-rays with a distribution (relative number of photons) per photon energy (frequency) determined by the energy of the incident electrons. A high voltage (V) input, V1, applied between the heated filament and the anode accelerates each electron before the electron slams into the anode. The kinetic energy of a single electron accelerated by a 1-volt electric field is an electron volt (about $1.6 \times 10^{-19}$ Joules, or $4.45 \times 10^{-24}$ kilowatt-hours). To produce x-rays, the voltage V1 is many tens of thousands of volts. The x-ray tube produces x-ray photons with a distribution of photon energies up to a cutoff photon energy determined by the input voltage V1; that is, all x-ray photons have energies less than or equal to a cutoff energy of V1 electron-volts (at cutoff frequency vc). The peak energy (at frequency vp) is the x-ray photon energy that has the most photons; the peak energy is slightly less than V1 electron-volts. The number of photons produced decreases with decreasing photon energy (frequency) below the peak energy (frequency vp).

The x-ray power supply 140 provides the high voltage input, V1, between the heated filament and the anode. The x-ray power supply 140 also provides enough electrons per second, current (I), to supply a useful number of electrons striking the anode. An Ampere of current is 1 coulomb per second, which is about $0.6 \times 10^{19}$ electrons per second. The power provided by the power supply is the product of the current I and the voltage V1. By definition, the unit of the product, an Ampere-volt, is a Joule per second, which by definition is 1 Watt.

In a dual-energy system, the power supply also drives the x-ray tube at a different voltage V2, which causes a different distribution of x-ray energies (frequencies) with a different cutoff energy (at a second cutoff frequency vc2) and a different peak energy (at a second peak frequency vp2).

The x-ray beam-forming component 135 includes a collimator 134 for shaping the beam angle 139 and a filter 136 for limiting the distribution of frequencies about the peak frequency. A monitor 137 is also included to measure x-ray characteristics of the source, as described in more detail below with reference to FIG. 4A.

The collimator is made of an x-ray opaque material, such as lead, with an opening (aperture) size and shape selected to give the beam 138a a particular cross section in a plane perpendicular to the centerline. The beam angle α, in the X-Z plane across subject 191, is typically larger than the beam angle β, in the plane containing the centerline of the beam 138a and perpendicular to the X-Z plane, along subject 191.

The filter is made of a material that blocks the lower energy x-rays, below the peak energy, passing only x-rays with energies above a high-pass energy (at frequency va). As a result, only a narrow range of x-ray photon energies, from a high pass energy (at va) just below the peak energy (at vp) to the cutoff energy (at vc), emerges from the x-ray source assembly 130. In a dual-energy system, a second filter is used when the power supply drives the x-ray tube at the second voltage V2. The second filter blocks x-ray photon energies below a second high pass energy (at va2), which is less than the second peak energy (at vp2).

The receiver assembly 150 includes a detector 152, an optional radial adjustment component 156, and an anti-scatter element, such as anti-scatter grid 154. The detector includes one or more receptors that respond to the x-ray fluence (energy per unit area). The diminution of fluence from the source assembly to a receptor in the detector along any radial line is due to geometrical spreading of the beam, which is easily calculated, and the absorption by the subject 191 and subject table 190. The absorption by the subject depends on the photon energy (frequency) of the beam and the material in the subject 191.

The anti-scatter element reduces the number of photons striking the detector from directions other than a radial direction to the detector from a focal point 133 in the x-ray tube. The material in subject 191 and table 190 absorbs some x-ray photons and scatters some in other directions. If these scattered photons strike the detector, the measured intensity is increased and the computed absorption is erroneously decreased. Estimates of scattering may be made to correct the computation of absorption, but the estimates are both difficult and imprecise. If the scattering can be reduced, both the speed and the precision of the absorption computation can be enhanced. The anti-scatter component is usually made up of an x-ray opaque material, such as lead, with slits aligned perpendicularly to the detector, so that only photons traveling on a perpendicular ray strike the detector 152. Such perpendicular slits eliminate much of the scattering in conventional DXA systems.

The radial adjustment component 156 allows the distance from the detector 152 to the subject 191 or focal point 133 or both to be changed. It is sometimes advantageous to change these distances. For example, decreasing the distance from subject 191 to detector 152, and increasing the radial distance from receiver assembly 150 to source assembly 130, may allow the entire subject to be imaged at one time. This is one way a full body scan of subject 191 is obtained. The system 100 would be re-calibrated whenever this distance is changed.

FIG. 1B is a block diagram illustrating the apparatus of FIG. 1A when configured for a different projection angle. In FIG. 1A the projection angle of the x-ray beam 138a from source assembly 130 to receiver assembly 150 is −90 degrees, as measured counterclockwise from a horizontal ray pointing to the right. The location of the −90 degree x-ray beam 138a is shown in FIG. 1B for reference. In the configuration of FIG. 1B, the gantry 122, with its fixed assemblies 130, 150, has been rotated 45 degrees counterclockwise by mechanisms in gantry base 101 under control of computer 160. In FIG. 1B the projection angle is −45 degrees. As a result, an x-ray beam 138b intersects a different portion of the subject 191. By rotating the gantry 122 45 degrees clockwise, another projection angle of −135 degrees, is obtained.

The portion 192 of subject 191 is illuminated by both beams 138a, 138b. Consequently data is obtained on bones in portion 192 of subject 191 for two projection angles, −90 degrees and −45 degrees.

According to some embodiments of the invention, the properties of the structural elements in system 100 are selected to provide more spatially detailed measurements of absorption than are available from conventional dual-energy x-ray absorptiometry (DXA) systems. For example a high-resolution detector is employed and a three-dimensional anti-scatter grid 154 is employed.

According to some embodiments of the invention, the properties of the structural elements in system 100 are selected to enhance portability of the system. For example, a smaller, more portable power supply than in the conventional DXA systems is used.

In addition, according to embodiments of the invention, the method of operating system 100 is modified to produce results that support the computation of structural strength of individual bones, unlike conventional DXA systems. For example, exposures at multiple projection angles are employed with overlapping beam volumes, and computer software is executed to form three-dimensional models of the bones, and to compute strength properties and risk of fracture based on the models. For another example, exposure time is controlled to maximize signal to noise ratio (SNR) using smaller, more portable power supplies.

2. AMPDXA Scanning System

According to an embodiment, an advanced, multiple-projection, dual-energy x-ray absorptiometry (AMPDXA) scanning system includes 1) a conical collimator; 2) a high-resolution two-dimensional detector; 3) a portable, power-capped, variable-exposure-time power supply; 4) an exposure-time control element; 5) calibration monitoring; 6) a three-dimensional anti-scatter-grid; and 7) a gantry-gantry base combination that permits up to seven projection angles for overlapping beams. No conventional DXA system known to the inventors includes these structural features, either in combinations of two or more, or alone (for some features). These features are described in more detail in separate sections below.

In addition, according to this embodiment, the AMPDXA is configured to use a low photon energy beam at 80 kV and a high photon energy beam at 140 kV. In other embodiments, the low photon energy beam is separated even more from the high photon energy beam to better distinguish bone minerals from soft tissue. For example, in some embodiments the low photon energy beam is at 50 kV.

In the embodiment using a low energy beam of 80 kV, the filter used with the 80 kV beam includes multiple layers of molybdenum and tungsten. A molybdenum layer of about 0.1 mm thickness is designed to minimize low photon-energy x-rays. A tungsten layer of about 0.25 mm thickness transmits x-rays having photon energies near the peak energy while attenuating x-rays with higher photon energies. The result is a beam with a narrow spectrum of photon energies. It is anticipated that the thickness of the filter materials and the voltage applied to the x-ray tube may be varied in other embodiments in order to further refine the spectrum to sharply distinguish bone from soft tissue or lean from fat tissue or both.

Figure 2A:
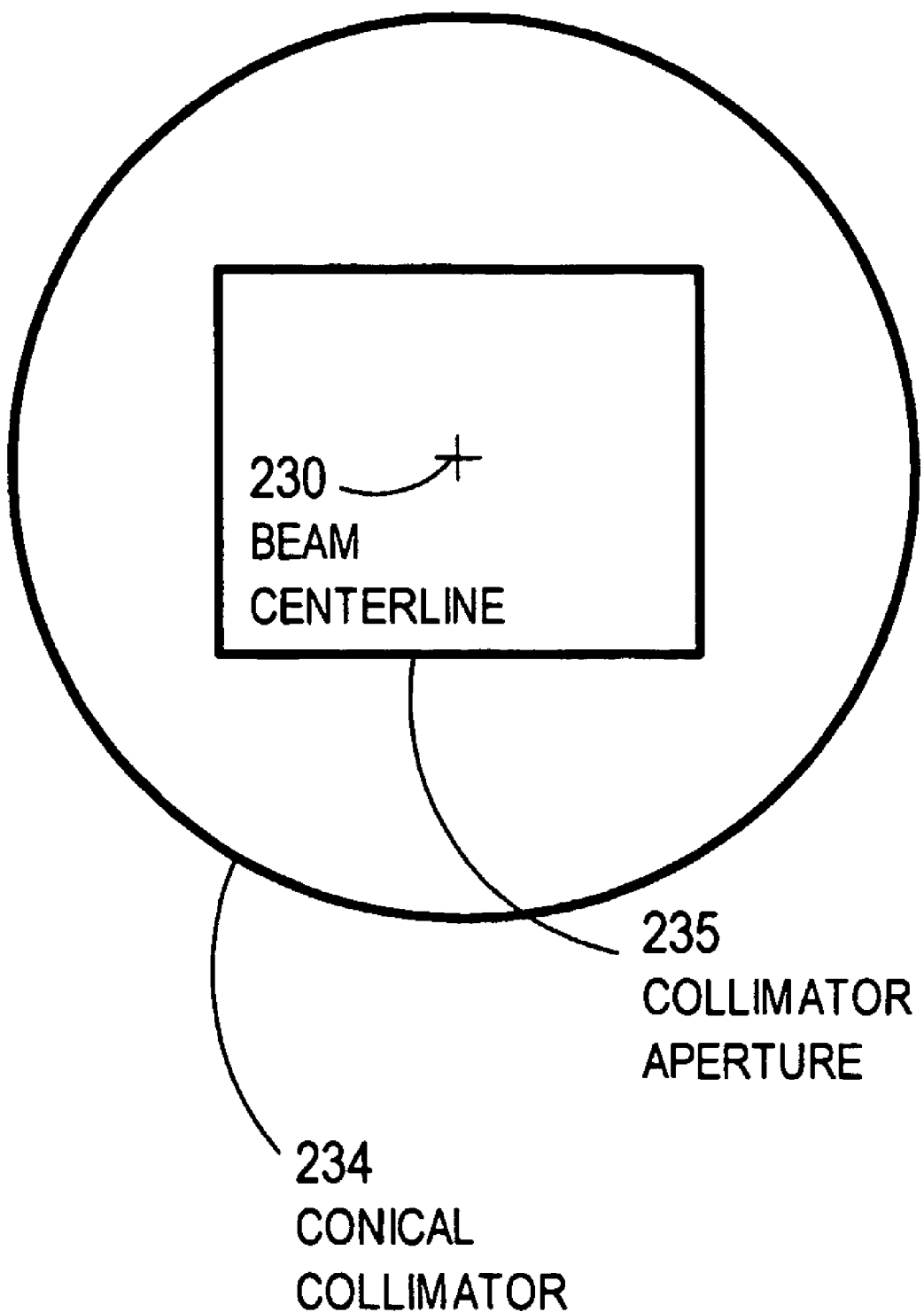
FIG. 2A is a block diagram illustrating a collimator for a conical beam for a dual-energy x-ray absorptiometry apparatus, according to an embodiment.

The filter used with the 140 kV beam includes multiple layers of gadolinium, molybdenum and copper. A molybdenum layer of about 1.0 mm thickness is designed to minimize low photon-energy x-rays. A gadolinium layer of about 0.2 mm thickness transmits x-rays having photon energies near the peak energy while attenuating x-rays with higher photon energies. In some embodiments a copper layer about 1 mm thick is included. The result is a high photon-energy beam with a narrow spectrum of photon energies. It is anticipated that the thickness of the filter materials and the voltage applied to the x-ray tube may be varied in other embodiments in order to further refine the spectrum to sharply distinguish bone from soft tissue or lean from fat tissue or both 2.1 Conical Collimator A conical beam is formed by placing a conical collimator in the beam-forming component 135. As used herein, a conical beam is any beam with a cross section that is two-dimensional, having a width commensurate with its length. FIG. 2A is a block diagram illustrating a collimator 234 for a conical beam for a dual-energy x-ray absorptiometry apparatus, according to an embodiment of collimator 134 in FIG. 1A. The view of FIG. 2A is in a plane perpendicular to the X-Z plane of FIG. 1A; the intersection of the X-Z plane would be a horizontal line in FIG. 2A going through the beam centerline 230. The collimator is made of an x-ray opaque material, such as lead, and includes an aperture 235 shaped according to the beam to be produced. The beam centerline 230 is defined by the center of the aperture 235. An aperture is used that matches the shape of the area detector. In the illustrated embodiment, the aperture 235 is rectangular because area detectors are typically rectangular. Using a circular or oval aperture with a rectangular detector would result either in a waste of detector surface or a waste of radiation dosage to a subject patient. The beam angle α 139 in the X-Z plane is determined by the size of the aperture in the X-Z plane and the distance from a focus point (133 in FIG. 1A) of the x-ray tube. The focus point 133 is a point from which the x-rays appear to be emanating when viewed at a position removed from the anode. The beam angle β in the unique plane perpendicular to X-Z plane and containing the centerline is determined by the size of the aperture perpendicular to the X-Z plane and the distance to the focus point.

Many conventional DXA systems use a slit aperture, which is much narrower than the rectangular aperture 235, to form a fan beam rather than a conical beam. By using a conical beam in the illustrated embodiment, more of the photons produced by the x-ray tube are included in the beam; thus making more efficient use of a limited power supply. For example, 75% more of the x-rays produced by the x-ray tube are used with a rectangular conical beam in the illustrated embodiment than are used in a fan beam.

2.2 High-resolution Area Detector

FIG. 2B is a block diagram illustrating an area detector 252 for a dual-energy x-ray absorptiometry apparatus, according to an embodiment of x-ray detector 152 in FIG. 1A. The area detector 252 has a length and width to substantially enclose the cross section (238) of the rectangular conical beam at the distance where the detector 252 is disposed in the receiver assembly (150 in FIG. 1A). The beam centerline intersects the detector at point 230. The width of the beam at the detector in the X-Z plane is indicated by double arrow 239 and the width of the beam at the detector in the perpendicular plane including the centerline is indicated by the double arrow 237.

The detector is configured with an array of receptors that respond to the fluence of impinging x-rays. Adjacent receptors distinguish fluence at adjacent locations. The highest resolution of the detector is determined by the size and separation of the pair of adjacent receptors, such as receptors 210a, 210b that constitute pair 212. The resolution is often expressed as the number of receptor pairs per millimeter (mm); the larger the number, the better the resolution.

Several detectors are known in the art. For example, many use scintillator materials, which produce visible light when struck by x-rays. The scintillator is coupled to an array of photodiodes. Conventional DXA systems use receptors arranged in one or two lines, with resolutions of 0.1 to 1 pairs per mm along each line. According to embodiments of the invention, detectors are used with resolutions of 2 or more pairs per millimeter. This provides improved resolution employed to produce structural models of bones that are not achievable with conventional DXA systems.

The receptors are arranged in rows. FIG. 2B shows a row 220a of receptors that includes several squares indicating receptors and ellipsis 213, which indicates additional receptors are included in the row. FIG. 2B shows rows 220a, 220b, 220c, 220d and ellipsis 223, which indicates additional rows of receptors are included in the detector. Conventional DXA systems use receptors arranged in one or two rows. According to the illustrated embodiment, the area detector 252 is filled with rows of receptors. By using an area detector that substantially enclosed the conical beam, more of the photons produced by the x-ray tube are utilized in measuring absorption by the subject; therefore, less power is wasted. In addition, less time is consumed to scan the subject because each exposure of the illustrated system images an area that takes tens or hundreds of exposures using conventional DXA systems. Furthermore, less complex scanning mechanisms can be employed because scanning steps need not be precise steps less than a millimeter in size.

Several area detectors are known in the art. For example, phosphor screen scintillators are known that produce visible light over a two dimensional area with intensity (number of photons per unit area) proportional to the fluence of x-rays. Arrays of light detectors, such as charge-couple devices (CCDs,) are used as the receptors. Each element of the array provides data for a pixel. A pixel is a picture element that makes up an image. The smaller the receptor, the more receptors can be packed into a given area and the greater is the resolution.

In the illustrated embodiment, a cesium iodide screen large enough to enclose the beam cross section 238 is used as the phosphor screen. In other embodiments, a variety of scintillator materials are used, including gadolinium oxysulfide and cesium iodide. The light detector is an amorphous silicon detector array.

In some embodiments, an amorphous semiconductor material is used in place of a scintillator. The amorphous semiconductor material absorbs impinging x-rays and produces free electrons, rather than visible light. In various embodiments, different amorphous semiconductor materials are used, including lead iodide, thallium bromide, thallium iodide and selenium, among others. The amorphous semiconductor silicon detector collects the resulting electrons.

In either set of embodiments, the receptors comprise an array of amorphous silicon detectors, which has 0.127-mm square pixels. That is, the amorphous silicon detector array has a receptor and gap between receptors that together are 0.127 mm across. The intensity at the pixel is a measure of the x-ray fluence along a path from the focus point, through the patient, to the receptor.

The resolution in the subject is typically even greater than the resolution at the detector because the x-rays diverge from the focus point to the receiver, and the subject lies between the focus point and the receiver. For example, if the subject is positioned at 80% of the distance from the focus point to the detector, then the pixels correspond to subject volume elements that are 80% of the size of the pixels in the detector. Therefore the resolution is about 1/(0.8) greater—about 25% greater in a plane through the subject.

Furthermore, amorphous silicon detector arrays are available that cover areas that are on the same scale as subject sizes. For example, amorphous silicon detector arrays are currently available in sizes of about 200 mm by 250 mm (about 8 inches by 10 inches); and anticipated increases extend this area to about 430 mm by 430 mm (about 17 inches by 17 inches). In an example embodiment, a 200 mm by 250 mm amorphous silicon detector array includes 1408 rows of 1888 receptors per row, each receptor a 0.127-mm square. This corresponds to a resolution of 3.8 pairs per mm. The increased resolution leads to more precise measurements of bone structures and more accurate models of bone properties. The large area leads to fewer exposures and simpler scanning mechanisms.

2.3 Power Supply

Conventional power supplies are too massive to be portable, including use in a space station. For example, typical exposures are expected to be about 7.5 milliAmperes seconds (mAs) at 80 kV (600 Joules, J) for the low photon-energy beam and about 4 mAs at 140 kV (560 J) for the high photon-energy beam. Conventional x-ray power supplies would involve peak powers of 5 to 20 kiloWatts (kW) to provide such beams. In addition, the peak currents or exposure time or both should be varied to account for different average absorption rates of different individuals so that the dynamic range between high and low intensity regions on the area detector matches the dynamic range of the instrument. Matching the dynamic range of the detector reduces the signal to noise ratio (SNR), as described in more detail below. Conventional power supplies with such features typically weigh too much to satisfy space flight specifications.

Figure 3A:
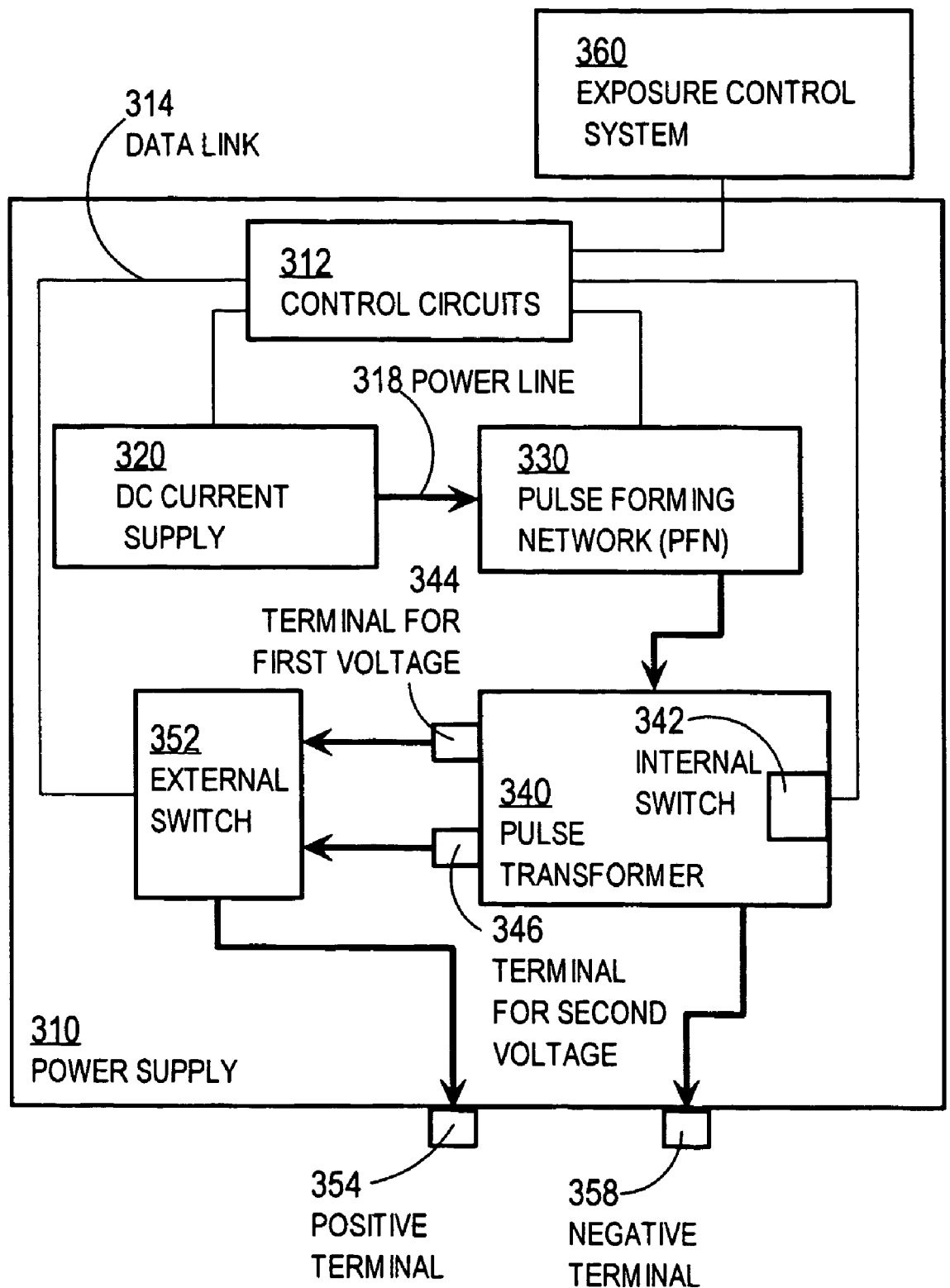
FIG. 3A is a block diagram illustrating a portable power supply for a dual-energy x-ray absorptiometry apparatus, according to an embodiment.

FIG. 3A is a block diagram illustrating a portable power supply 310 for a dual-energy x-ray absorptiometry apparatus, according to an embodiment. This power supply breaks up a high voltage pulse for the x-ray tube into many short pulses of constant magnitude, which can be separated in time sufficiently to reduce peak power consumption (Pmax) to levels that can be provided by smaller, more portable components. Portable direct current supplies of a favorable size and weight are available for peak powers of about 0.5 kW and less.

The power supply 310 includes a direct current (DC) current supply 320 sending direct current over a power line, as indicated by arrow 318, to a pulse forming network (PFN) 330. For example the DC current supply provides current Is at voltage Vs such that the product $Is*Vs \leq Pmax$. DC current supplies for Pmax less that 0.5 kW and Vs about ten kiloVolts are well known in the art.

The PFN includes one or more capacitors to store charges at voltages about ten kiloVolts and to form a series of constant pulses. Each pulse has a constant current Ip and a constant voltage Vp. Each pulse has pulse duration Tp and is repeated at a pulse time interval Ti. To keep power usage below Pmax, Tp and Ti are selected so that the following relationship holds:

$$Ip Vp * Tp/Ti > Pmax \quad (1)$$

In preferred embodiments, the pulse voltage Vp is about 10 kV rather than the full x-ray anode voltage, 80 kV and 140 kV, to reduce the size and cost of the components, such as capacitors, in the PFN. It is well within the skill of those in the art of power supplies to form a PFN having the characteristics described. For example, distributed inductance and several capacitors are connected to create a lumped constant transmission line. The electrical length of the line is made to be one half the desired pulse width. The line impedance (ratio of voltage to current) is made to match the impedance of the x-ray tube reflected on the primary terminal of the pulse transformer. The capacitance C (ratio of electric charge to voltage) is made to store the amount of energy used in each pulse. For example, if the capacitors are charged to a voltage Vc, then the capacitance C satisfies the relationship in equation 2:

$$0.5 * C * Vc^2 = Vp * Ip * Tp \quad (2)$$

The PFN may be formed in any manner known at the time the power supply is built.

FIG. 3B is a timeline chart illustrating output current and voltage from PFN 330 for the portable power supply 310, according to an embodiment. Time increases with distance along time axis 362. Voltage is graphed against time as a voltage trace 333 using the voltage axis 364. The voltage is at a minimum voltage, represented by position 331 on the voltage axis, between pulses; and rises to a maximum voltage, represented by position 332 on the voltage axis, during the pulse. The pulse duration Tp is indicated by the horizontal bar 338. The pulse interval Ti is represented by the horizontal bar 339. Current is graphed against time as a current trace 337 using the current axis 366. The current is at a minimum current, represented by position 335 on the current axis, between pulses; and rises to a maximum current, represented by position 336 on the current axis, during the pulse. For example, the minimum voltage is zero, the maximum voltage is 10 kV, and the minimum current is zero. If Tp is 0.1 milliseconds (ms) and Ti is 1.1 ms, then, using the above expression, the power is less than 300 W if the pulse current Ip is $Ip<300*1.1/(0.1*10,000)$ $Ip<330$ mAs.

Note that the allowed pulse power (Ip*Vp=3,300 W) is 11 times larger than Pmax, reflecting the factor of 11 between the pulse duration Tp and the pulse interval Ti.

The pulses are input to a pulse transformer 340 over another power line. The pulse transformer 340 steps up the voltage of the PFN output to the required x-ray tube voltage. In the illustrated embodiment, the pulse transformer includes an internal switch 342, which selects circuitry to step up the PFN voltage output by one factor for the low photon-energy beam and selects circuitry to step up the PFN voltage output by a larger factor for the high photon-energy beam. For example, circuitry stepping up voltage by a factor of 8 to terminal 344 is selected to produce the 80 kV beam; and circuitry stepping up voltage by a factor of 14 to terminal 346 is selected to produce the 140 kV beam. It is well within the skill of those in the art of power supplies to form a pulse transformer having the characteristics described. The pulse transformer may be formed in any manner known at the time the power supply is built.

The illustrated power supply 310 includes an external switch 352 to direct the output from the proper terminal to a positive terminal 354 that is connected to the anode of the x-ray tube. The negative terminal 358 receives the electrons extracted from the positive terminal for connection to the heated filament of the x-ray tube.

In the illustrated embodiment, the components of the power supply are controlled by one or more control circuits 312 connected to the DC current supply 320, the PFN 330, the pulse transformer 340 and the external switch 352 by data links 314. For example, the control circuits 312 turn the DC current supply on and off in response to input from an exposure control system 360. In the illustrated embodiment, the exposure control system 360 is external to the power supply 310; in other embodiments, the exposure control system 360 is partially or completely included in the power supply 310. The control circuits 312 also determine which beam is to be produced and therefore control internal switch 342 in the pulse transformer 340 and the external switch 352 to create and direct the proper anode voltage to the positive terminal 354. In some embodiments, the pulse duration Tp and pulse interval Ti are adjustable by the control circuits 312 based on determinations made internally, or by exposure control system 360, or by an external computer system (e.g., computer system 160 in FIG. 1A).

The power consumed by the x-ray tube should not exceed the power supplied by the DC current supply, 320 and the PFN 330. Thus the product of the voltage at the positive terminal 354 and the current composed of electrons collected by the anode must be less than the power provided. This ratio of voltage to current is the impedance of the pulse transformer as viewed by the PFN. For example, for a PFN having Pmax of 200 W and a ratio of Ti to Tp of ten, the pulse current, Ip, at 80 kV is 25 mA and the impedance is $3.2 \times 10^6$ V/A. The pulse current at 140 kV is 14.3 mA and the impedance is greater, at $9.8 \times 10^6$ V/A.

The anode in the x-ray tube 132 tends to crack if at low temperatures when subjected to high-energy electron beams. Warm-up currents are therefore made. This process is simple in ground-based systems where peak powers Pmax of 80 to 100 kW are routine; but such warm-up currents are not easily achieved with a low weight power supply. Instead, according to embodiments of the invention, a second cathode in the x-ray tube, used to produce large focal spots on the anode, is powered with a warm-up current at less than 300 W for about a minute. Most x-ray tubes use two cathode structures permitting a large and small electron beam at the anode target surface. The large spot is not used to produce the high-resolution images of the illustrated embodiments; but is useful for slowly warming the anode. For example a one-minute exposure at 3 mA and 80 kV to 90 kV will warm up the anode.

The warm-up power will be provided by a DC current supply without a PFN or pulse transformer. In one embodiment, the DC power supply is switched into the circuit for the second (large focal spot) cathode to warm up the anode and then turned off and switched out by high voltage contactors when the x-ray tube is properly prepared for diagnostic exposures.

2.4 Exposure Control

The distribution of photons emitted by the x-ray tube depends on the driving voltage between the anode and filament and on the filter; but, at a given voltage, the number of photons generated per unit time depends on the current. The low power pulses generated by the portable power supply 310 carry less current than conventional DXA systems, therefore fewer photons are produced, and fewer x-ray photons reach the detector per unit time.

The noise level at the detector 152 is determined by the number of visible light photons (or free electrons) collected per pixel during data acquisition over the full exposure time. Noise decreases with an increase in the square root of the number of photons collected divided by the average number of photons per pixel over the whole detector. Noise is therefore inversely proportional to the detected fluence. To decrease the noise it is best to increase the fluence by increasing the number of pulses and hence the exposure time. However, signal is lost if the exposure time is increased so long that the dynamic range (difference between highest recordable intensity and lowest recordable intensity) is exceeded. To maximize the signal to noise ratio (SNR) at the detector, it is best to expose the detector to only enough pulses that the brightest pixels are about at the maximum recordable intensity value. A target fluence at the detector associated with an adequate SNR near the maximum SNR is determined during calibration.

An individual subject may often deviate significantly from the average subject. Absorption of x-rays increases exponentially with subject thickness. Therefore the fluence of x-rays at the detector decreases exponentially with subject thickness and the noise increases exponentially. These deviations are significant from one individual to the next. Thus, according to embodiments of the invention, exposure time, expressed in seconds or number of pulses, is adjusted based on the fluence of x-ray photons measured for the individual at the detector.

Figure 4A:
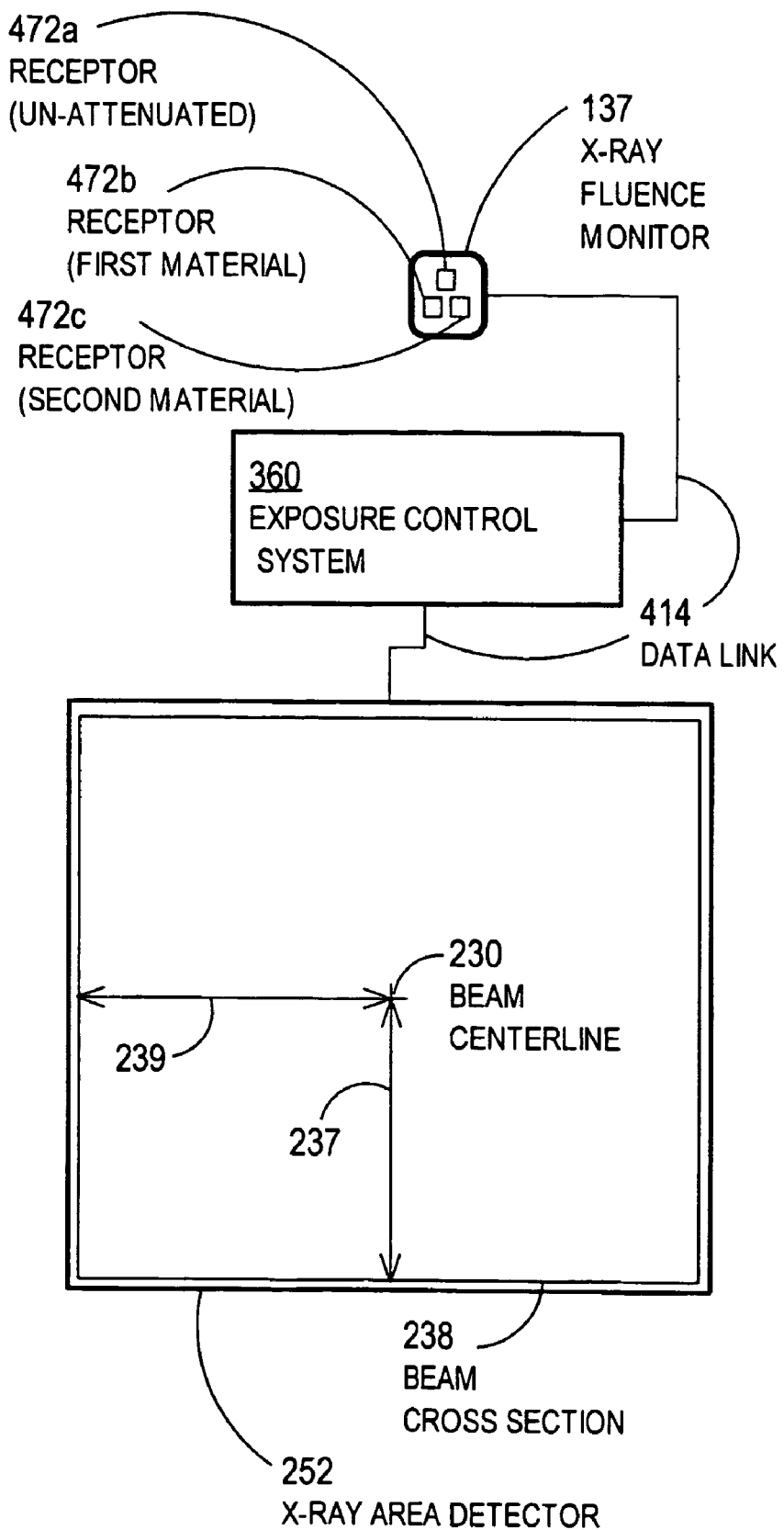
FIG. 4A is a block diagram illustrating a fluence detector that provides input to an exposure control system for the portable power supply, according to an embodiment.

FIG. 4A is a block diagram illustrating a fluence detector that provides input to an exposure control system for the portable power supply, according to an embodiment. The exposure control system 360 is connected by a data link 414 with an x-ray area detector 252 and an x-ray fluence monitor 137. The use of the x-ray fluence monitor 137 is described in more detail in the next section with respect to monitoring calibration.

The beam centerline intersects the detector 252 at point 230. The width of the beam at the detector in the X-Z plane is indicated by double arrow 239 and the width of the beam at the detector in the perpendicular plane including the centerline is indicated by the double arrow 237. According to embodiments of the invention, the exposure control system 360 receives data from one or more receptors of the area detector 252 for each of one or a few pulses. The data are used as a test exposure to compute the fluence at detector 252 per pulse. The predetermined target fluence desired for the adequate SNR is divided by the computed fluence per pulse to determine the number of pulses and hence the exposure time.

In some embodiments, the exposure time (or the number of pulses) is computed based on an average attenuation and the x-ray fluence emerging from the source assembly. In such embodiments the x-ray fluence at the source is measured with a first receptor 472a in an x-ray fluence monitor 137 placed in the beam forming component. Attenuation is computed based on the ratio of the fluence at the source measured at receptor 472a and the fluence at the detector 252 using equation 3, described below.

In some embodiments, the exposure control system 360 turns off the power supply when the computed number of pulses has been fired.

According to many embodiments, the intensity measured by the detector 252 at the end of the exposure includes the photons used in the test exposure. Thus the subject is not exposed to any extra radiation in order to determine the exposure time. The computation of bone mineral density at each pixel is determined based on the intensity images generated With average subjects and x-ray tube efficiency in converting electron energy to x-ray energy, it is expected that, at 80 kV, about 3000 pulses of duration 0.1 ms provide adequate SNR. With pulse intervals of 1 ms, this amounts to about 3 seconds. At 140 kV, about 2800 pulses of duration 0.1 ms provide adequate SNR, amounting to 2.8 seconds. It is anticipated that target subjects, such as astronauts and patients being screened, will be immobilized with a positioning device that rigidly holds the scanned limb during such exposure times.

2.5 Calibration Monitoring

DXA methods measure attenuation through a subject for each pixel in the image formed of the subject at the detector. Attenuation H is computed according to equation 3.

$$H = -\ln(Fs/F0) \quad (3)$$

where ln is the natural logarithm function, Fs is the fluence at the pixel with the subject present and F0 is the fluence at the pixel without the subject present. These two values cannot be recorded simultaneously. In some approaches, the value of Fs is determined by making an exposure with the subject present and F0 is determined by making a similar exposure at a later time with the subject absent. However, the characteristics of the x-ray tube may not be identical at the two times. Beam characteristics are sensitive to small changes in the driving voltages that can often occur.

According to embodiments of the invention, a fluence monitor 137 is placed in the beam-forming component 135 (FIG. 1A) to determine F0 simultaneously with the measured quantity Fs. The fluence monitor 137 is located between the filter 136 and the collimator 134 so as not to block the aperture in the collimator. Fluence is recorded at that point over the same exposure time as is used to generate the image at the detector 252. The fluence at the detector without the subject, F0, is then computed by computing the radial spreading of the x-ray beam from the distance of the fluence monitor to the distance of the detector.

According to embodiments of the invention depicted in FIG. 4A, the fluence monitor 137 includes three receptors, 472a, 472b, 472c, collectively referenced as fluence monitor receptors 472. One fluence monitor receptor 472a measures the fluence without attenuation. One fluence monitor receptor 472b measures the fluence as attenuated through a thickness of a first calibration material; and one fluence monitor receptor 472c measures the fluence as attenuated through a thickness of a second calibration material. The two calibration materials simulate bone and soft tissue. For example, a specific alloy of aluminum, well known in the DXA art, is used to simulate bone, and Plexiglas is used to simulate soft tissue. In some embodiments, the data indicating fluence at the fluence monitor receptors are sent to the exposure control system 360, as illustrated. In other embodiments, the data are sent to the computer system 160 for the computation of tissue masses.

The fluence monitor receptor with a calibration material, 272b, 272b determines whether small variations in the beam characteristics include variations in the distribution of x-ray photon energies in the beam, which affect attenuation in the calibration materials. These measurements greatly enhance the precision of the attenuation measurements and improve the validity of the bone strength and injury risk computations.

DXA methods are based on the assumption that x-ray images acquired at two photon-energies can be decomposed into equivalent images. Each equivalent image indicates the thickness of one of two known basis materials, herein called calibration materials. Calibration involves imaging of calibration phantoms each consisting of a set of orthogonal thicknesses of a calibration material. According to these methods, attenuation at each photon-energy is a polynomial function of the thicknesses of the two calibration materials. The coefficients of the polynomial are determined by measurements on the phantoms. The polynomial functions are inverted to yield the thickness of each calibration material as a polynomial function of the attenuations at the two photon-energies. Results are acceptable, when the calibration materials have attenuations that differ in a way similar to the difference between the subject tissues, and when the range of thicknesses of the phantom objects correspond to the range of thicknesses of the tissues that are encountered in the subject. For example, aluminum or calcium phosphate tribasic type IV is used as a calibration material corresponding to bone, and acrylic (methyl methacrylate) or Plexiglas is used as a calibration material corresponding to soft tissue. A pixel including only soft tissue can be decomposed into fat and lean tissue using phantom objects made of 0.6% sodium chloride solution as a calibration material corresponding to lean tissue, and stearic acid as a calibration material corresponding to fat tissue.

FIG. 4B is a block diagram illustrating two phantom objects used together to calibrate the x-ray absorption measurements and check the exposure control system, according to an embodiment.

In the illustrated embodiment, the soft tissue phantom object 491 includes 11 thicknesses of acrylic in 25.4 mm steps from 0 to 254 mm. The thicknesses occur between five top surface segments 493a, 493b, 493c, 493d, 493e (collectively called top surface 493) and six bottom surface segments 492a, 492b, 492c, 492d, 492e, 492f (collectively called bottom surface 492). The greatest thickness, 254 mm, occurs between bottom surface segment 492a and top surface segment 493*a*. The next greatest thickness occurs between the same top surface segment 493*a* and the next bottom surface segment 492*b*. The steps between segments on the bottom surface are staggered from the steps between segments on the top surface so that two thicknesses are associated with each surface segment (except 492*a*).

In the illustrated embodiment, the hard (bone) tissue phantom object 496 includes 7 thicknesses of aluminum in 5 mm steps from 0 to 30 mm. The thicknesses occur between three top surface segments 498*a*, 498*b*, 498*c* (collectively called top surface 498) and four bottom surface segments 497*a*, 497*b*, 497*c*, 497*d* (collectively called bottom surface 497). The greatest thickness, 30 mm, occurs between bottom surface segment 497*a* and top surface segment 498*a*. The next greatest thickness occurs between the same top surface segment 493*a* and the next bottom surface segment 497*b*. The steps between segments on the bottom surface are staggered from the steps between segments on the top surface so that two thicknesses are associated with each surface segment (except 497*a*).

The hard tissue phantom object 496 may be placed on one of the top or bottom surface segments of soft tissue phantom object 491, as indicated by arrow 499 to obtain calibration data for two acrylic thicknesses and 7 aluminum thicknesses (14 combinations) in one image. A total of 77 combinations of thicknessses can be obtained in seven images. The 77 combinations are used to deduce coefficients relating attenuations at two photon-energies to thicknesses of two calibration materials.

In other embodiments, a soft tissue phantom object comprises five thicknesses of plastic from 50 mm to 250 mm in increments of 50 mm, and a bone tissue phantom object comprises five thicknesses of aluminum of about 1.5 mm, 6 mm, 13 mm, 19 mm, and 38 mm.

In some embodiments, the phantom objects are also used to determine the target fluence associated with an adequate SNR.

2.6 Anti-scatter Grid

In some embodiments, a pair of high-quality anti-scatter slit grids are used. The slits of one grid are disposed to be perpendicular, in the horizontal X-Y plane, to the slits of the second grid. The pair reduces scattering compared to a single grid made of slits of aluminum interspersed with slits of lead with a ratio of aluminum slit width to lead slit width of 10 to 1.

In conventional DXA systems that use line detectors comprising one or two rows of receptors, scattering is effectively reduced by very narrow slits and fan or pencil x-ray beams. The detectors are so limited in area that scattered rays do not reach the detector. However, with a conical beam and an area detector, scattered rays can have a more significant effect, especially at the center of the area detector. Pixels in the center of the area detector receive scatter from a larger angle of emission subtended by the volume of the irradiated subject. In conventional radiography, anti-scatter grids are used; but the conventional radiographic images are more qualitative. The calibration of the AMPDXA system is invalidated by scattering that is tolerable for conventional radiography. To minimize the effect on attenuation measurements, intensity of scattered x-rays should not be more than about a few percent of the unscattered intensity at any pixel in the image.

Anti-scatter grids are usually made with holes or channels aligned along the paths of the unscattered x-rays with walls, or septra, between the openings made of heavy metals like lead, tantalum and tungsten to absorb the scattered rays striking the walls. Making the holes or channels deeper reduces the acceptance angle of scatter. Making the walls between the openings thick improves the absorption of scatter but present a larger cross section that blocks more of the unscattered beam and obscures more details in the image. A grid composed of elongated channels is less effective than one composed of holes because the channels do not exclude scattered x-rays aligned within planes parallel to the channels. However, a grid composed of channels is easier to fabricate. Most anti-scatter grids are made with channels between thin lead walls. To support the lead, the channels are usually filled with aluminum or plastic material, which absorbs some of the unscattered x-rays and reduces overall effectiveness.

An ideal grid would be made of holes, focused to the x-rays source, made with very thin walls of a heavy metal. The walls should be thin enough to be invisible on the image, but thick enough to effectively absorb the scattered rays.

Further reduced scatter, and hence increased precision in measurements of absorption, is obtained with an advanced two-dimensional grid. The grid is designed to pass only x-rays that are within a maximum acceptance angle θmax from perpendicular. The maximum acceptance angle is made as small as possible, preferably less than 1 degree. Openings are formed in a thin lead sheet, or foil. The size O of the opening and the thickness T of the sheet determine the θmax of x-rays that pass through the grid according to the equation $$\tan(\theta max)=O/T \tag{4}$$

The openings are kept small enough to prevent x-rays impinging at angles greater than θmax. In some embodiments the T is 10 to 20 times the size O of the opening.

The lead walls between openings can interfere with the horizontal resolution of the area detector. If the walls are wide compared to the horizontal resolution, then one or more receptors are blocked by the lead wall. Therefore the advanced two-dimensional grid has openings so closely spaced that the lead walls are less wide, i.e., have a smaller distance, than the horizontal resolution of the area detector. For example, with an area detector having 0.127-mm receptors, the lead walls should be less wide than 0.127 mms.

In some embodiments a three-dimensional anti-scatter grid is formed that reduces scatter still further, especially at the outer edges of the area detector. The three-dimensional anti-scatter grid is formed so that, when placed in the receiver assembly 150, the upper surface of the grid, the surface facing the x-ray source, lies substantially on a surface of a sphere having a center at a source point of the x-ray beam (also called the focal spot of the x-ray tube). For example, the three-dimensional anti-scatter grid is formed to lie on a sphere having a radius of about one meter, by attaching the lead foil with openings to a Plexiglas plate shaped with a one-meter radius of curvature, as shown in FIG. 5. When configured in this way, the x-rays that originate at the focal spot of the x-ray tube are detected while x-rays coming at angles that only arise during scattering are substantially blocked.

In FIG. 5 a thin lead sheet 530 is formed with openings 510*a*, 510*b* arranged in rows 520*a*, 520*b*, 520*c* of openings. The lead sheet is chosen to be large enough to cover the area detector. For example, the lead sheet is chosen to be 432 mms (about 17 inches) long by 432 mms wide. The ellipsis 513 indicates many additional openings are formed in each row 520*a* of openings. The ellipsis 523 indicates many additional rows are formed on the lead sheet 530. The number of openings per row and the number of rows are selected to cover the area detector. For example, the lead sheet 530 is filled with openings. To make the grid as thick as possible in some embodiments multiple sheets are perforated, machined, and subsequently stacked.

The width of the lead wall between openings, for example between openings 510a and 510b, is chosen to be small with respect to the horizontal resolution of the area detector. For example, the width of the walls is chosen to be less than 0.127 mms.

The anti-scatter grid must be smooth to minimize or prevent unpredictable artifacts on the image, such as blockage by shards of metal. That is, the roughness of the outer lead surface should be small compared to the size of the opening on space scales as short as the width of the lead walls between openings. The outer lead surface includes the top surface of the grid, facing the x-ray tube when disposed in the receiver assembly, and includes the sidewalls of the openings. Roughness is a measure of the root mean square deviations in distance of a surface from an average position over a particular length scale. The maximum opening length is the diagonal of the square openings shown in FIG. 5. Thus roughness small compared to this opening is roughness less than a particular small fraction of this distance, such as about 0.1 percent of this distance.

Figure 5B:
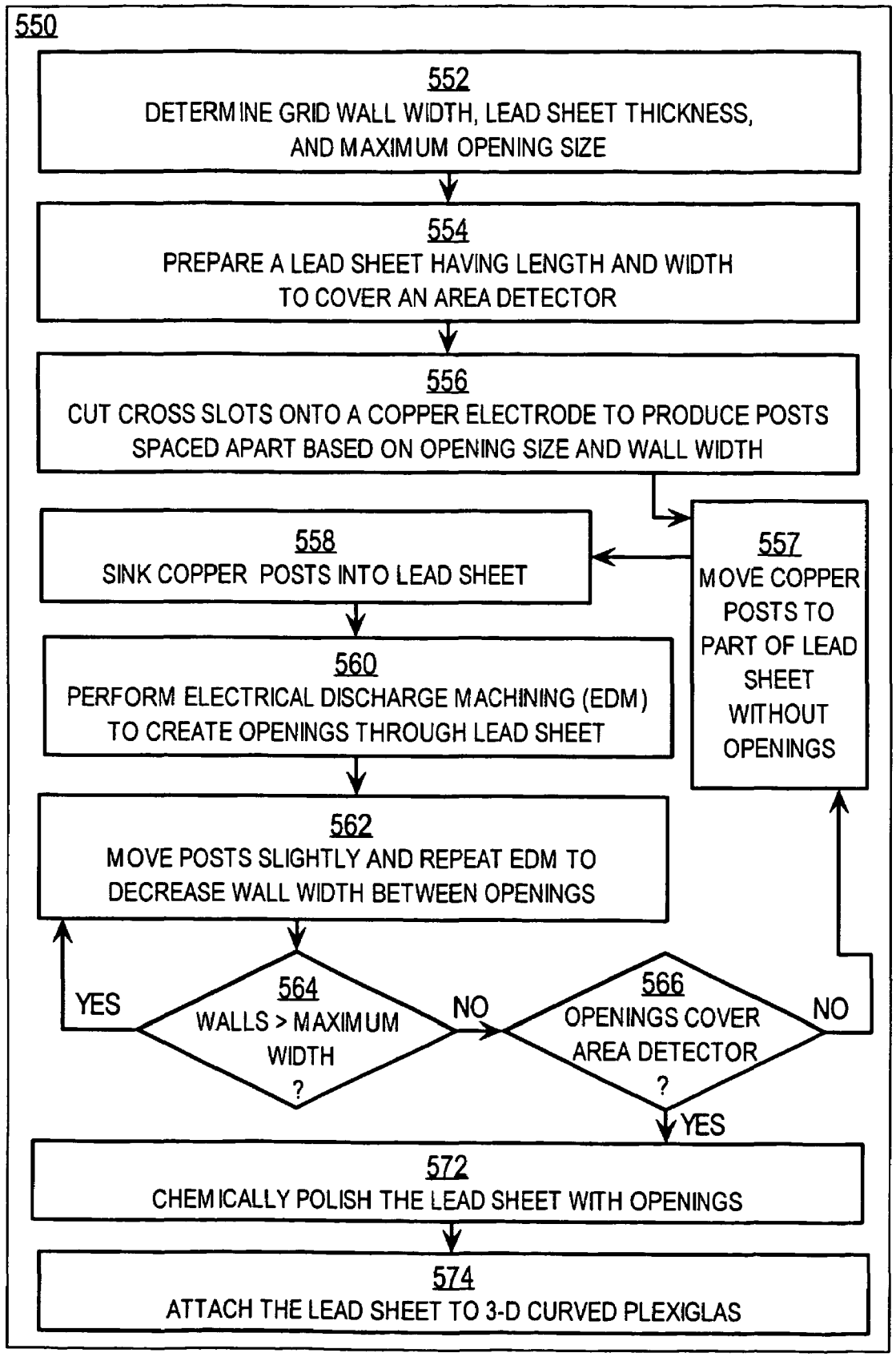
FIG. 5B is a flow chart illustrating at a high level a method for fabricating the three-dimensional anti-scatter grid, according to an embodiment.

FIG. 5B is a flow chart illustrating at a high level a method 550 for fabricating the three-dimensional anti-scatter grid of FIG. 5A, according to an embodiment. Although steps are shown in a particular order in FIG. 5B and other flow charts, in other embodiments the steps can be reordered or occur overlapping in time.

In step 552, the grid wall width is determined to be smaller than the horizontal resolution of the area detector, the lead sheet thickness is chosen to be thick enough to substantially block x-rays that hit sidewalls of the openings, and the maximum opening size is selected to block deviation angles greater than θmax. For example, the thickness is chosen to be 2.5 mm, and the opening size chosen to be a square less than about 0.068 mm on a side (for a maximum acceptance angle from perpendicular of about 1.56 degrees). The grid wall width is chosen to be about the horizontal resolution of the area detector, 0.127 mm, or less.

In step 554 a lead sheet of the chosen thickness is prepared that is long enough and wide enough to cover the area detector. For example a 99.9% pure lead sheet of thickness 2.5 mm (about 0.10 inches) is produced.

In step 556 cross-slots are cut onto a copper electrode to produce posts of substantially square cross section, which are regularly spaced at a distance interval (pitch) substantially equal to the sum of the opening size and the wall width determined in step 552. For example, the copper electrode is made by cutting 0.254-mm (0.010 inches) wide cross slots that are each 2.03 mm (0.080 inches) deep on a 0.762-mm (0.030 inches) pitch along one direction and then another using a wire electrical discharge machining (EDM) device. This produces electrodes with an array of approximately 1,000 0.50-mm (about 0.020 inch) square posts per square inch (per 645 mm$^2$). An electrode with 3,000 such posts has been produced. Control then passes to step 557.

In another embodiment, wire EDM is employed in step 556 to cut 0.127-mm (0.005 inches) wide cross slots that are each 2.03 mm (0.080 inches) deep on a 0.762-mm (0.030 inches) pitch. The electrode is filled with molten lead and allowed to solidify. Then the copper is chemically removed, leaving a lead structure with walls 0.127 mm wide and 2 mm deep. Then control passes to step 572 to attach the lead structure to the flat or curved support plate, as described in more detail below.

In step 557, the copper posts are moved to a portion of the lead sheet without openings. In step 558, the copper posts are die sunk into the malleable lead sheet. For example, the copper electrode with posts is die sunk into a corner of the lead sheet using a die sinking EDM.

In step 560, EDM is performed to burn holes through the lead foil. For example square openings of 0.5 mm (about 0.02 inches) length and width are burned through the 2.5 mm thick lead sheet. This leaves wall about 0.25 mm wide between the openings.

In step 562 the openings are made wider to decrease the width of the walls separating the openings. This is accomplished by programming the EDM device for an x-axis/y-axis orbiting function. In step 562 it is determined whether the walls have been reduced enough. For example it is determined whether the walls are about 0.127 mm wide or less. If so, control passes to step 566. If not, the step 562 is repeated until the walls are thinner than or equal to the maximum width. For example, the walls are reduced from widths of 0.254 mm to widths of 0.127 mm and the openings increased to 0.627-mm squares.

In step 566, it is determined whether openings cover enough of the lead sheet to pass x-rays to essentially the entire area detector. If not, control passes to step 557 to move the copper posts to another portion of the lead sheet, currently without openings. Steps 558, 560, 562, 564 are repeated to produce openings in the new section.

It is expected that openings with cell walls as narrow as 0.1 mm can be formed in lead sheets or foils as thick as about 10 mm. Small patterns of openings can be reproduced over areas as large as about 60,000 mm$^2$.

Figure 5C:
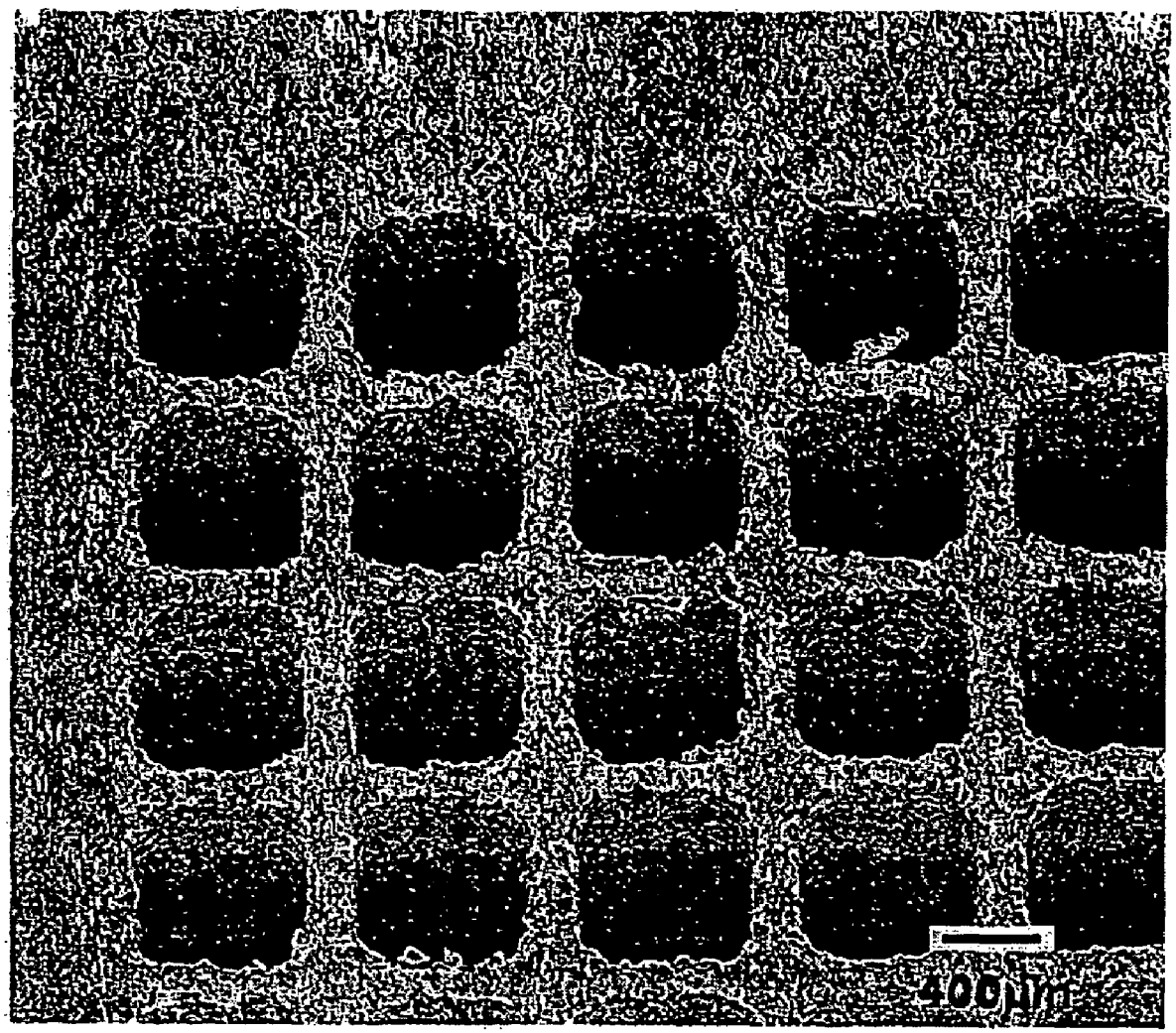
FIG. 5C shows a micrograph of some openings in a lead sheet before chemical polishing, according to an embodiment.
Figure 5D:
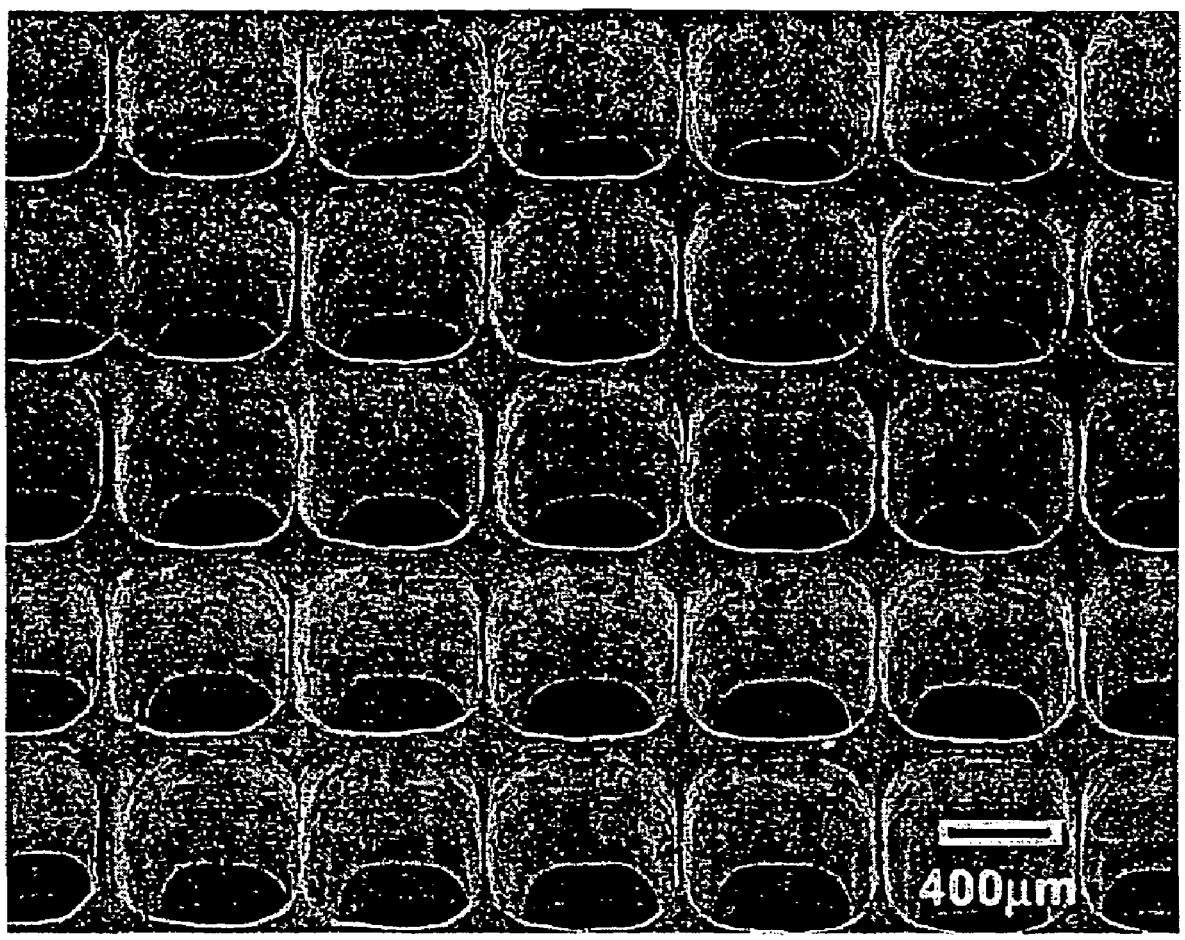
FIG. 5D shows a micrograph of similar openings in a lead sheet after chemical polishing, according to an embodiment.

If it is determined in step 566 that the openings cover enough of the lead sheet, then control passes to step 572. In step 572, the lead sheet with the openings is chemically polished to reduce roughness. For example, a mixture of 1 part hydrogen peroxide with four parts of acetic acid diluted to 10% with water is formed. This is approximately 10 parts hydrogen peroxide to about 4 parts acetic acid to about 36 parts water. The lead sheet is submerged in the mixture at room temperature for about three minutes. FIG. 5C shows a micrograph of some openings in a lead sheet after EDM and before chemical polishing. FIG. 5D shows a micrograph of similar openings in a lead sheet after chemical polishing. The roughness of the outer lead surfaces is much reduced after chemical polishing.

In step 574 the chemically polished lead sheet is attached to a material that is transparent to x-rays and that can support the lead sheet in position in the receiver assembly 150. For example, the lead sheet with openings is attached to a flat Plexiglas plate to form a two-dimensional anti-scatter grid. In some embodiments a Scotchweld 2216 adhesive is employed to attach the lead sheet to the Plexiglas plate. In a preferred embodiment, the chemically polished lead sheet with openings is attached to a Plexiglas plate shaped for a three dimensional anti-scatter grid. The malleable lead sheet readily conforms to many smooth surfaces. For example, the lead sheet is attached to a Plexiglas plate shaped as a portion of a sphere with a radius of curvature that matches the distance from a focal spot in the x-ray tube to the surface of the lead sheet when disposed in the receiver assembly. For example, the Plexiglas plate has radius of curvature of about one meter.

2.7 Multiple Projection Gantry

The gantry is configured to so that beams at multiple projection angles illuminate a particular volume in a subject. Three projections of the same bone are often adequate to form useful 3-D models. The use of three projection angles may not be adequate in cases where there are two bones in the volume, such as in the forearm and lower leg. Simulations indicate that five projections are adequate in those cases. Thus, in some embodiments, the gantry is configured to allow at least five intersecting beams at five projection angles.

To model the hip, in some embodiments, the subject table is configured to rotate to image in a plane including the hip bone neck-shaft angle. In some embodiments, seven projection angles are used to model the hip bone.

The gantry is also configured to acquire a whole body bone mineral density image. In some embodiments this is accomplished by using a detector and beam width wide enough to sample the entire subject in the X-Z plane for at least some positions of the subject table.

The 3-D modeling is expected to provide useful information for many additional applications besides bone strength. For example, the system can be used to construct the spatial relationship between bones and metal objects implanted in the patient for repair or as prosthetics. Such spatial relationships may evidence separation and loosening of the metal objects at an early stage before complete failure.

3. Methods for Operating AMPDXA

Figure 6A:
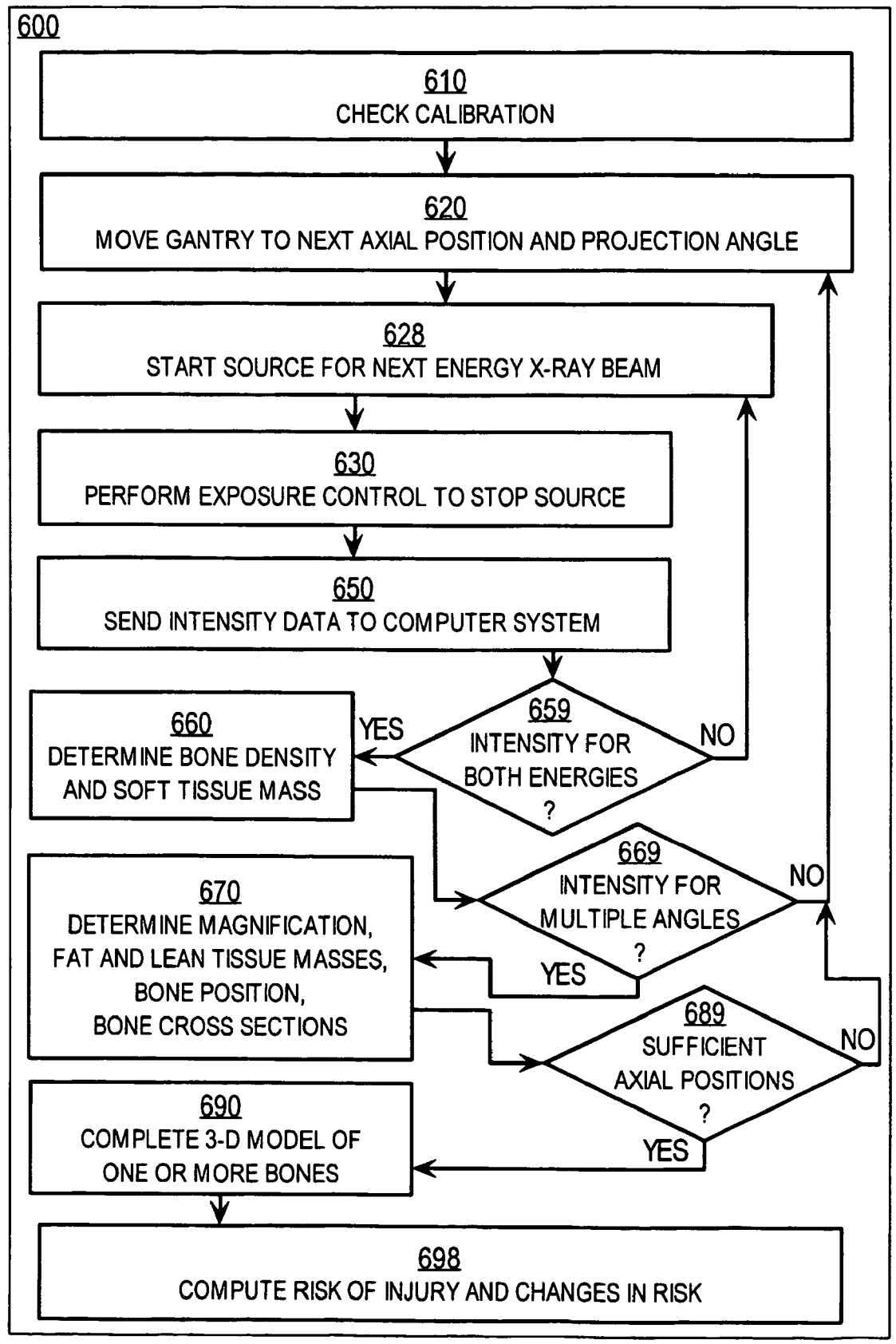
FIG. 6A is a flow chart illustrating at a high level a method for operating a multiple-projection dual-energy x-ray absorptiometry apparatus, according to an embodiment.

FIG. 6A is a flow chart illustrating at a high level a method 600 for operating a multiple-projection dual-energy x-ray absorptiometry apparatus, according to an embodiment. Although steps are shown in a particular order in FIG. 6A and FIG. 6B, in other embodiments the steps can be reordered or occur overlapping in time.

In step 610, the calibration is determined. For example, one or both phantom objects are placed on the subject table and attenuation measurements are made at both photon energies. During initial calibration, attenuations at the two photon energies are used with the known thicknesses of the phantom objects to derive coefficients of a polynomial relationship. During calibration checks, thicknesses are derived from the attenuation measurements and the coefficients, and the calculated thicknesses are compared with the known thicknesses of the phantom object or objects.

In some embodiments, step 610 includes checking data from fluence monitor 137. For example, the fluences at the receptors 472b, 472c with calibration materials are checked to determine whether either or both the fluences have changed. A change at receptors 472b, 472c indicates a change in beam characteristics that might affect calibration. If the changes are small, corrections are applied to the data collected at detector 252. If the beam characteristics have changed sufficiently, then a new calibration with phantom objects is performed.

In step 620, the subject on the subject table and gantry are positioned to acquire an image at the next axial position and projection angle. For example, initially a patient subject 191 is positioned on the subject table 190 so that the long axis of a bone to be scanned is approximately aligned with the Y dimension and the region to be scanned is centered on the beam center intersection with the subject table 190. In some embodiments laser alignment devices are used. The patient limb is immobilized with a positioning device. The initial projection angle is also set. For example a projection angle of −90 degrees clockwise from horizontal is set. In some embodiments, step 620 includes moving the subject table toward the receiver assembly to obtain an image that encompasses the entire width of the subject as part of a whole body scan.

For example, if three projection angles are to be imaged, step 620 includes moving the gantry to a first projection angle of the three initially. In subsequent visits to step 620, the gantry is moved to a second or third projection angle of the three projection angles. If additional portions of the subject in the Y dimension are to be imaged, in a subsequent visit, the subject table or gantry is moved in the Y direction to the next position.

In step 628, the source for the next photon-energy beam is started. If no beam has yet been imposed on the subject, the next energy beam is one of the two or more photon energies. If a first energy beam has been imposed on the subject, then another of the two or more photon-energy beams are started. For example, exposure control system 360 sends a signal to control circuit 312 in power supply 310 to form pulses at the driving voltages across terminals 354 and 358 for the next photon-energy beam.

Figure 6B:
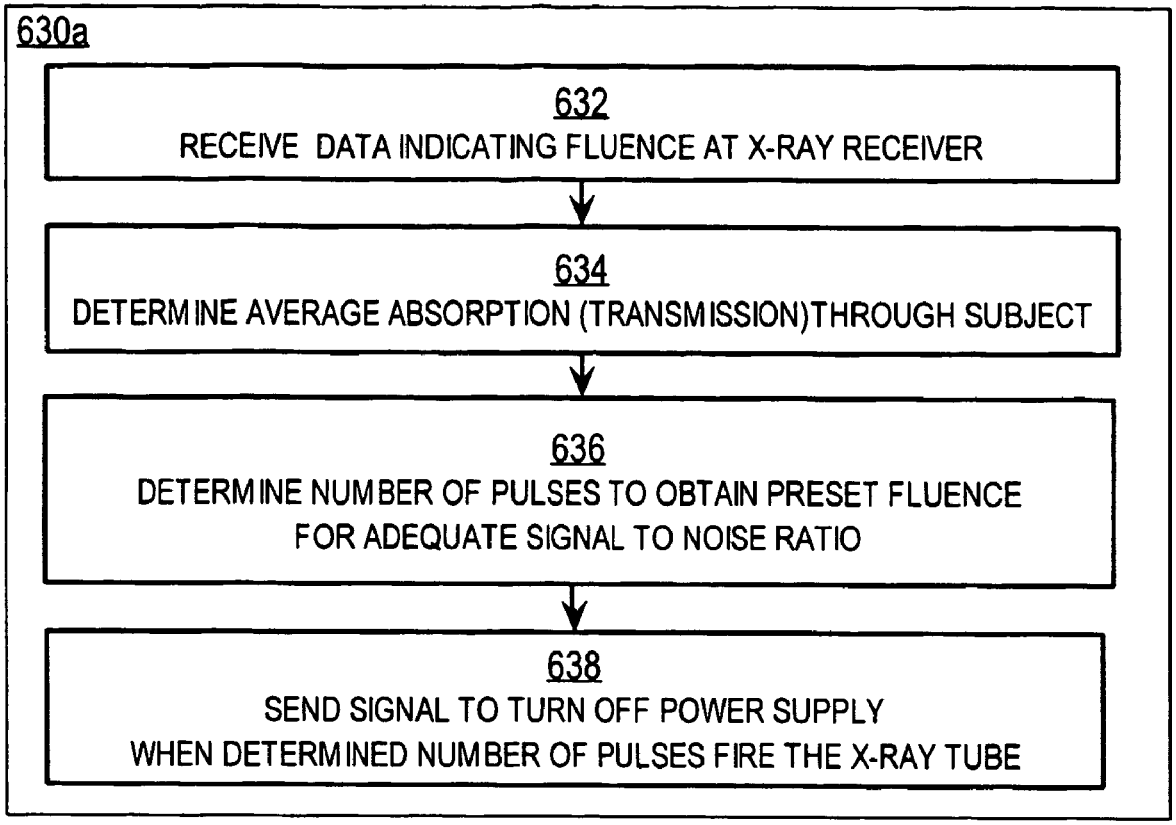
FIG. 6B is a flow cart illustrating details of a step of the flow chart of FIG. 6A, according to an embodiment.

In step 630, exposure control is performed to determine when to stop the source for the current beam. FIG. 6B is a flow cart illustrating details of an embodiment 630a of step 630 of the method 600 of FIG. 6A.

In step 632, data is received by an exposure control system 360, such as an exposure control process running on computer system 160. The data indicates fluence of x-rays at the x-ray detector up to a particular time. For example, data indicating visible photon intensity at substantially all receptors of an amorphous silicon detector array are received up to a time corresponding to 10 pulses of 1 microsecond duration from the beam source assembly. In some embodiments, only data from receptors in a central portion of the area detector 252 are received.

In step 634, the average attenuation through the subject is computed. In some embodiments this includes correcting the visible photon intensity at each pixel for geometric spreading from a spherical intensity front to the flat detector surface, for estimated scattering, and for glare using procedures well known in the art. In these embodiments, the intensity so corrected is divided by the intensity computed based on the measured fluence at the fluence monitor 137. Attenuation H is computed using equation 3. In some embodiments, the attenuation is averaged over pixels only in a central portion of the area detector.

In step 636 the exposure time is computed to achieve the target fluence and predetermined adequate SNR. For example, the number of pulses for the current photon-energy beam is computed by dividing the target fluence by a function of the average attenuation and the beam fluence computed for the detector based on the fluenc monitor 137. In some embodiments, the number of pulses for both the current photon-energy beam and the next photon-energy beam is computed. In such embodiments, step 636 can be omitted during the exposure control of the next photon-energy beam.

In step 638 a signal is sent to turn off the power supply when the number of pulses determined in step 636 have been fired. In one embodiment, the exposure control system sends a signal to the power supply stop when the number of pulses have been received. In another embodiment, the number of pulses is sent to the control circuit 312 of the power supply 310, and the control circuit 312 stops after the determined number of pulses.

In step 650, intensity data is sent to computer system 160 to compute the attenuation image. In some embodiments step 650 includes computing attenuation for the current photon-energy beam. For example, the intensity data corrected for flat-field, scatter and glare at each pixel is divided by the fluence data at fluence monitor 137 corrected for geometrical spreading to the flat detector, and the negative natural log of the result, according to Equation 3, is sent as an attenuation value for the pixel. In some embodiments, the computation is performed by computer system 160. In other embodiments, the computation of attenuation is performed during step 660, described below.

In step 659, it is determined whether both photon energy beams have been imposed on the subject. If not, control passes to step 628 to start the source for the next photon-energy beam. If so, control passes to step 660 to determine bone mineral density and soft tissue mass at each pixel. Step 659 can be performed in any manner known in the art. For example, step 659 can be a branch point in a software program in one embodiment, a circuit switch in another embodiment, or a choice by a human operator in another embodiment.

In step 660, the two attenuations at the two photon-energies for each pixel and the calibration data are used to decompose two thicknesses for each pixel. For example, bone thickness and soft tissue thickness are computed. If no bone is available in the pixel, then, in some embodiments, thicknesses for fat and lean tissue are determined based on the two attenuations. In some embodiments, step 660 includes computing bone mineral density and soft tissue mass in units of mass per unit area (grams per square centimeter) based on the thickness and the known density of such tissue. In other embodiments, bone mineral density and soft tissue mass are computed in a later step.

In step 669, it is determined whether both photon energy beams have been imposed on the subject at all projection angles. If not, control passes to step 620 to move the gantry to the next projection angle. If so, control passes to step 670 to determine tissue properties that can be deduced from multiple projection angles. Step 669 can be performed in any manner known in the art. The number of projection angles depends on operational choices for the particular bone being scanned. Three projections spanning at least 90 degrees angular separation are often sufficient. Where multiple bones appear in one or more of the first three projections additional projections are used, for example five projections are used. In difficult areas, such as the human hip, even more projections may be used.

In step 670 tissue properties deduced from multiple angles are computed. For example, bone position relative to source and receiver assemblies positions can be deduced. The bone position determines the distance from bone to detector and therefore the magnification factor for bone structural features. Thus bone mineral cross sections can be produced with the correct magnification corrections. In addition, paths that do not intersect bone can be used to determine how much of the soft tissue mass is lean and how much is fat for use in pixels at other projections that include some bone mass. This allows images to be generated at each projection that accurately subtract soft tissue for pixels that include bone attenuation. Because each pair of exposures produces an two-dimensional image, bone orientation, width, cross sectional areas and moments of inertia can be computed at several points along the long axis of the bone.

In step 689, it is determined whether images have been obtained at a sufficient number of axial positions. If not, control passes to step 620 to move the gantry or subject table to obtain an image at the next axial position. If so, control passes to step 690 to determine tissue properties that can be deduced from multiple axial positions. Step 669 can be performed in any manner known in the art. The number of axial positions depends on operational choices for the particular bone being scanned. Often a single axial position suffices. For example, if the entire bone to be scanned appears in the image, no further axial positions are needed and control passes directly to step 690. In a whole body scan, for example, several axial positions are usually involved even if the area detector is large enough to image the entire width of the subject in the X-Z plane.

In step 690 tissue properties deduced from the one or more axial positions are computed. For example, principal moments of inertial for an entire bone can be derived. From the principal moments of inertia a three dimensional (3-D) model with patient specific mechanical properties is derived. Control then passes to step 698.

In step 698, estimates of risk of injury, including risk of bone breakage are computed. For example, estimates of mechanical strength, scaled for body size, gender and other factors, are computed. In some embodiments, step 698 includes determining the spatial relationship between bones and metal objects implanted in the patient for repair or as prosthetics. Such spatial relationships may evidence separation and loosening of the metal objects at an early stage before complete failure.

In some embodiments 3-D models and risk of injury are computed and stored at several different times that are days, weeks, months, or years apart. In such embodiments, differences in mechanical properties and risks of injury may be computed. In some embodiments, step 698 includes determining the efficacy of countermeasures for bone loss based on such changes in risk over time.

4. Computer Hardware Overview

Figure 7:
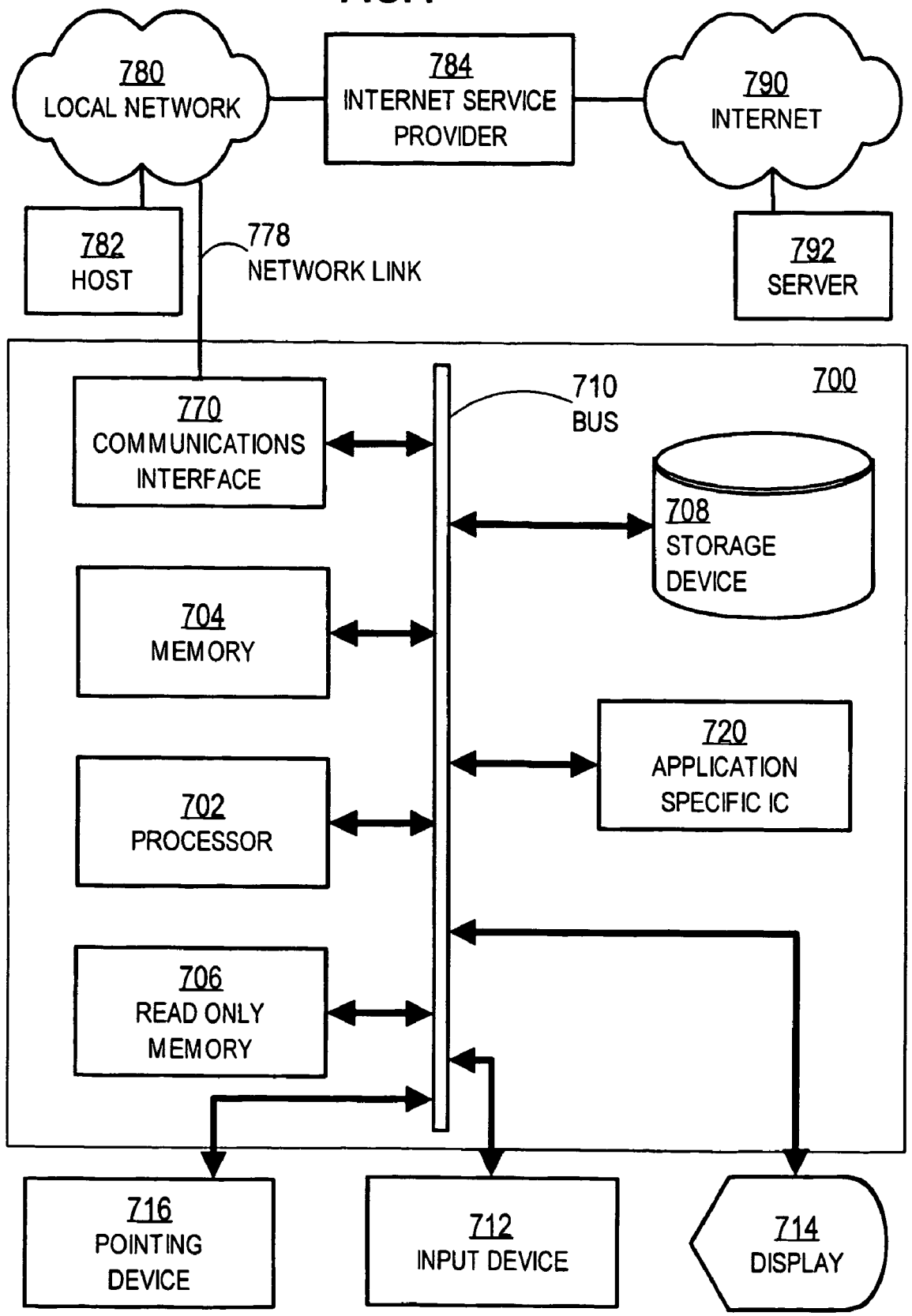
FIG. 7 is a block diagram that illustrates a computer system upon which an embodiment of some steps in FIG. 6A may be implemented.

FIG. 7 is a block diagram that illustrates a computer system 700 upon which an embodiment of some processes of the invention may be implemented. Computer system 700 includes a communication mechanism such as a bus 710 for passing information between other internal and external components of the computer system 700. Information is represented as physical signals of a measurable phenomenon, typically electric voltages, but including, in other embodiments, such phenomena as magnetic, electromagnetic, pressure, chemical, molecular and atomic interactions. For example, north and south magnetic fields, or a zero and non-zero electric voltage, represent two states (0, 1) of a binary digit (bit). A sequence of binary digits constitute digital data that is used to represent a number or code for a character. A bus 710 includes many parallel conductors of information so that information is transferred quickly among devices coupled to the bus 710. One or more processors 702 for processing information are coupled with the bus 710. A processor 702 performs a set of operations on information. The set of operations include bringing information in from the bus 710 and placing information on the bus 710. The set of operations also typically include comparing two or more units of information, shifting positions of units of information, and combining two or more units of information, such as by addition or multiplication. A sequence of operations to be executed by the processor 702 constitute computer instructions.

Computer system 700 also includes a memory 704 coupled to bus 710. The memory 704, such as a random access memory (RAM) or other dynamic storage device, stores information including computer instructions. Dynamic memory allows information stored therein to be changed by the computer system 700. RAM allows a unit of information stored at a location called a memory address to be stored and retrieved independently of information at neighboring addresses. The memory 704 is also used by the processor 702 to store temporary values during execution of computer instructions. The computer system 700 also includes a read only memory (ROM) 706 or other static storage device coupled to the bus 710 for storing static information, including instructions, that is not changed by the computer system 700. Also coupled to bus 710 is a non-volatile (persistent) storage device 708, such as a magnetic disk or optical disk, for storing information, including instructions, that persists even when the computer system 700 is turned off or otherwise loses power.

Information, including instructions, is provided to the bus 710 for use by the processor from an external input device 712, such as a keyboard containing alphanumeric keys operated by a human user, or a sensor. A sensor detects conditions in its vicinity and transforms those detections into signals compatible with the signals used to represent information in computer system 700. Other external devices coupled to bus 710, used primarily for interacting with humans, include a display device 714, such as a cathode ray tube (CRT) or a liquid crystal display (LCD), for presenting images, and a pointing device 716, such as a mouse or a trackball or cursor direction keys, for controlling a position of a small cursor image presented on the display 714 and issuing commands associated with graphical elements presented on the display 714.

In the illustrated embodiment, special purpose hardware, such as an application specific integrated circuit (IC) 720, is coupled to bus 710. The special purpose hardware is configured to perform operations not performed by processor 702 quickly enough for special purposes. Examples of application specific ICs include graphics accelerator cards for generating images for display 714, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 700 also includes one or more instances of a communications interface 770 coupled to bus 710. Communication interface 770 provides a two-way communication coupling to a variety of external devices that operate with their own processors, such as printers, scanners and external disks. In general the coupling is with a network link 778 that is connected to a local network 780 to which a variety of external devices with their own processors are connected. For example, communication interface 770 may be a parallel port or a serial port or a universal serial bus (USB) port on a personal computer. In some embodiments, communications interface 770 is an integrated services digital network (ISDN) card or a digital subscriber line (DSL) card or a telephone modem that provides an information communication connection to a corresponding type of telephone line. In some embodiments, a communication interface 770 is a cable modem that converts signals on bus 710 into signals for a communication connection over a coaxial cable or into optical signals for a communication connection over a fiber optic cable. As another example, communications interface 770 may be a local area network (LAN) card to provide a data communication connection to a compatible LAN, such as Ethernet. Wireless links may also be implemented. For wireless links, the communications interface 770 sends and receives electrical, acoustic or electromagnetic signals, including infrared and optical signals, that carry information streams, such as digital data. Such signals are examples of carrier waves.

The term computer-readable medium is used herein to refer to any medium that participates in providing instructions to processor 702 for execution. Such a medium may take many forms, including, but not limited to, non-volatile media, volatile media and transmission media. Non-volatile media include, for example, optical or magnetic disks, such as storage device 708. Volatile media include, for example, dynamic memory 704. Transmission media include, for example, coaxial cables, copper wire, fiber optic cables, and waves that travel through space without wires or cables, such as acoustic waves and electromagnetic waves, including radio, optical and infrared waves. Signals that are transmitted over transmission media are herein called carrier waves.

Common forms of computer-readable media include, for example, a floppy disk, a flexible disk, a hard disk, a magnetic tape, or any other magnetic medium, a compact disk ROM (CD-ROM), or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read.

Network link 778 typically provides information communication through one or more networks to other devices that use or process the information. For example, network link 778 may provide a connection through local network 780 to a host computer 782 or to equipment 784 operated by an Internet Service Provider (ISP). ISP equipment 784 in turn provides data communication services through the public, world-wide packet-switching communication network of networks now commonly referred to as the Internet 790. A computer called a server 792 connected to the Internet provides a service in response to information received over the Internet. For example, server 792 provides information representing video data for presentation at display 714.

The invention is related to the use of computer system 700 for implementing the techniques described herein. According to one embodiment of the invention, those techniques are performed by computer system 700 in response to processor 702 executing one or more sequences of one or more instructions contained in memory 704. Such instructions, also called software and program code, may be read into memory 704 from another computer-readable medium such as storage device 708. Execution of the sequences of instructions contained in memory 704 causes processor 702 to perform the method steps described herein. In alternative embodiments, hardware, such as application specific integrated circuit 720, may be used in place of or in combination with software to implement the invention. Thus, embodiments of the invention are not limited to any specific combination of hardware and software.

The signals transmitted over network link 778 and other networks through communications interface 770, which carry information to and from computer system 700, are exemplary forms of carrier waves. Computer system 700 can send and receive information, including program code, through the networks 780, 790 among others, through network link 778 and communications interface 770. In an example using the Internet 790, a server 792 transmits program code for a particular application, requested by a message sent from computer 700, through Internet 790, ISP equipment 784, local network 780 and communications interface 770. The received code may be executed by processor 702 as it is received, or may be stored in storage device 708 or other non-volatile storage for later execution, or both. In this manner, computer system 700 may obtain application program code in the form of a carrier wave.

Various forms of computer readable media may be involved in carrying one or more sequence of instructions or data or both to processor 702 for execution. For example, instructions and data may initially be carried on a magnetic disk of a remote computer such as host 782. The remote computer loads the instructions and data into its dynamic memory and sends the instructions and data over a telephone line using a modem. A modem local to the computer system 700 receives the instructions and data on a telephone line and uses an infra-red transmitter to convert the instructions and data to an infra-red signal, a carrier wave serving as the network link 778. An infrared detector serving as communications interface 770 receives the instructions and data carried in the infrared signal and places information representing the instructions and data onto bus 710. Bus 710 carries the information to memory 704 from which processor 702 retrieves and executes the instructions using some of the data sent with the instructions. The instructions and data received in memory 704 may optionally be stored on storage device 708, either before or after execution by the processor 702.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A multiple-projection, dual-energy x-ray absorptiometry apparatus comprising:
    a first source of a first conical beam of x-rays having photon energies in a first range of photon energies;
    a second source of a second conical beam of x-rays having photon energies in a second range of photon energies different from the first range of photon energies, the second beam co-located with the first beam;
    an x-ray receiver comprising an area x-ray detector for detecting x-ray intensity at a plurality of receptors distributed over an area having a length and a width;
    a subject table substantially transparent to x-rays;
    means for moving the first source, the second source, and the x-ray receiver sequentially around the subject table to at least three positions,
    wherein the first conical beam and the second conical beam intersect the subject table at at least three projection angles corresponding to the at least three positions and impinge on the area x-ray detector to provide a pair of images at each of the at least three projection angles for each of one or more longitudinal positions along a subject; and
    means for constructing a three-dimensional model of a bone based on the at least three pairs of images.

2. An apparatus as recited in claim 1, wherein bone mass in a subject on the subject table is determined within one percent for each receptor of the plurality of receptors.

3. An apparatus as recited in claim 1, the x-ray receiver further comprising a two dimensional anti-scatter grid with a plurality of holes.

4. An apparatus as recited in claim 1, the x-ray receiver further comprising a three dimensional anti-scatter grid with a plurality of holes.

5. An apparatus as recited in claim 1, wherein a distance from the first source to the area x-ray detector is about one meter.

6. An apparatus as recited in claim 1, wherein the area x-ray detector includes a plurality of pairs of adjacent receptors that distinguish x-ray intensity, the pairs of adjacent receptors arranged with more than two receptor pairs per millimeter.

7. An apparatus as recited in claim 6, wherein the pairs of adjacent receptors are arranged with at least 3.8 receptor pairs per millimeter.

8. An apparatus as recited in claim 1, wherein the area x-ray detector includes a plurality of receptors that measure x-ray intensity, the plurality of receptors arranged in more than two rows of receptors, each row including at least a hundred receptors.

9. An apparatus as recited in claim 1, wherein the area x-ray detector comprises an amorphous silicon detector.

10. An apparatus as recited in claim 9, wherein the width is at least 200 millimeters and the length is at least 200 millimeters.

11. An apparatus as recited in claim 9, wherein the amorphous silicon detector includes an array of 0.127-millimeter square receptors.

12. An apparatus as recited in claim 11, wherein the array includes at least 1400 rows of receptors and at least 1400 receptors per row.

13. An apparatus as recited in claim 1, further comprising a power supply for driving an x-ray tube at a selectable one of a first voltage and a second voltage, wherein:
    the first source comprises the power supply and the x-ray tube powered with the first voltage; and
    the second source comprises the power supply and the x-ray tube powered with the second voltage.

14. An apparatus as recited in claim 13, wherein the power supply has a mass less than about 10 kilograms and provides a voltage at the x-ray tube in a range from about 50 kiloVolts (kV) to about 150 kV.

15. An apparatus as recited in claim 1, wherein the first source comprises:
    an x-ray tube;
    a power supply providing a voltage of about 80 kilovolts between a cathode and an anode of the x-ray tube: and
    a filter comprising molybdenum and tungsten.

16. An apparatus as recited in claim 1, wherein the first source comprises:
    an x-ray tube: and
    a power supply providing a voltage of about 50 kiloVolts between a cathode and an anode of the x-ray tube.

17. An apparatus as recited in claim 1, wherein the second source comprises:
    an x-ray tube;
    a power supply providing a voltage of about 140 kiloVolts between a cathode and an anode of the x-ray tube; and
    a filter comprising gadolinium, molybdenum and copper.

18. A method for operating a multiple-projection, dual-energy x-ray absorptiometry apparatus, the method comprising:
    obtaining a pair or images sequentially at each of at least three projection angles for each of one or more longitudinal positions along a subject, a first image of the pair obtained using a first source of x-rays having a first range of photon energies and a second image of the pair obtained using a second source of x-rays having a second range of photon energies; and
constructing a three-dimensional model of a bone based on the at least three pairs of images obtained during said obtaining step.

19. The method of claim 18, further comprising computing risk of injury based on the three-dimensional model of the bone.

* * * * *